# United States Patent [19]

Nagoh et al.

[11] Patent Number: 6,110,400
[45] Date of Patent: Aug. 29, 2000

[54] FULGIMIDE COMPOUND AND USE THEREOF AND COMPOSITION CONTAINING SAID COMPOUND

[75] Inventors: Hironobu Nagoh; Junji Momoda; Tsuneyoshi Tanizawa, all of Tokuyama, Japan

[73] Assignee: Tokuyama Corporation, Yamaguchi-ken, Japan

[21] Appl. No.: 09/125,855

[22] PCT Filed: Dec. 26, 1997

[86] PCT No.: PCT/JP97/04876

§ 371 Date: Aug. 26, 1998

§ 102(e) Date: Aug. 26, 1998

[87] PCT Pub. No.: WO98/29414

PCT Pub. Date: Jul. 9, 1998

[30] Foreign Application Priority Data

Dec. 27, 1996 [JP] Japan ................................... 8-350286
Oct. 2, 1997 [JP] Japan ................................... 9-269467

[51] Int. Cl.$^7$ ............................ G02B 5/23; C07D 207/00
[52] U.S. Cl. .......................................... 252/586; 548/407
[58] Field of Search ............................ 252/586; 548/407

[56] References Cited

U.S. PATENT DOCUMENTS 4,882,438 11/1989 Tanaka et al. .
5,130,058 7/1992 Tanaka et al. ............................ 252/586
5,683,628 11/1997 Mizuno et al. ............................ 252/586

FOREIGN PATENT DOCUMENTS 60-155179 8/1985 Japan .
1-38063 2/1989 Japan .
64-90286 4/1989 Japan .
2-28154 1/1990 Japan .

Primary Examiner—Philip Tucker

[57] ABSTRACT

A novel fulgimide compound in which the nitrogen atom of the imide ring is substituted by a phenyl group having an electron-attracting group at least at the meta position, which is represented by the following general formula (I):

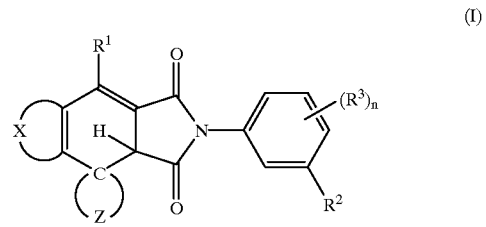

[wherein the group (a) of the following formula is a divalent aromatic hydrocarbon group or unsaturated heterocyclic group, each of which may have a substituent(s);

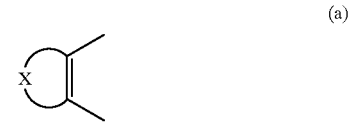

the group (b) of the following formula is a norbornylidene, bicyclo[3.3.1]nonylidene or adamantylidene group,

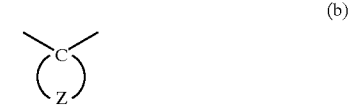

and $R^2$ is an electron-attracting group] and its use as a photochromic material.

The fulgimide compound of the present invention has a higher color density in a color-developed state than conventional photochromic compounds.

16 Claims, 1 Drawing Sheet

FULGIMIDE COMPOUND AND USE THEREOF AND COMPOSITION CONTAINING SAID COMPOUND

TECHNICAL FIELD

The present invention relates to a novel fulgimide compound having a photochromic action and to its use. More specifically, it relates to a novel fulgimide compound which changes its color from a colorless state to a colored state, the color change being reversible, when irradiated with a light containing ultraviolet rays, such as sunlight or light from a mercury lamp, and which has excellent durability, and to its use.

BACKGROUND ART

Photochromism is a phenomenon which has drawn attention for the last several years, and refers to a reversible action in which a certain compound rapidly changes its color when irradiated with a light containing ultraviolet rays, such as sunlight or light from a mercury lamp and returns to its original color when the irradiation is stopped and the compound is placed in a dark place. Compounds having this property are called photochromic compounds. Photochromic compounds of various structures have been synthesized and proposed, but no particular common skeleton has been observed in the structures.

Understanding the above background, JP-A Sho 60-155179 discloses a photochromic compound represented by the following general formula:

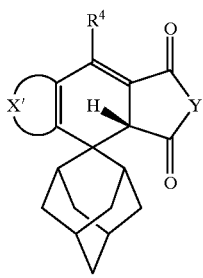

[wherein the group

is an aromatic group, an unsaturated heterocyclic group, or a heterocyclic group in which a benzene ring is fused; and
$R^4$ is a hydrogen atom, an alkyl group, an aryl group, an aralkyl group or a heterocyclic group;
Y is an oxygen atom or $$\diagup_{NR,}$$

(wherein R is a hydrogen atom, an aryl group, an alkyl group or an aralkyl group)] and its use in a photoreactive lens.
The following compound is disclosed in the Examples of this literature as a specific photochromic compound:

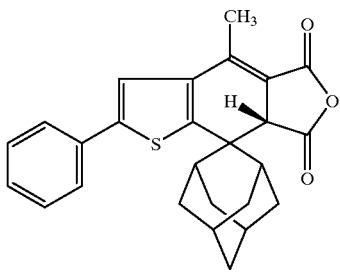

Also, JP-A Hei 2-28154 and U.S. Pat. No. 4,882,438 corresponding thereto disclose a fulgide or fulgimide compound represented by the following general formula:

[wherein the group $$\diagup_{X''}\diagdown$$

is a divalent aromatic hydrocarbon group or a divalent unsaturated heterocyclic group each of which may have a substituent (s); $R^5$ is a monovalent hydrocarbon group or a monovalent heterocyclic group each of which may have a substituent(s); the group $$\diagup_{Z'}\diagdown$$

is a norbornylidene group or an adamantylidene group each of which may have a substituent(s); and Y' is an oxygen atom,

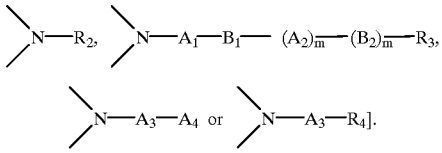

The fulgide or fulgimide compound has an excellent photochromic property because it remains stably colorless under normal condition, quickly develops a color when irradiated with sunlight or ultraviolet rays, returns to a colorless state when the irradiation is stopped, and repeats the above color change with good durability. The following compound is disclosed in the Examples of this literature as a specific fulgide or fulgimide compound:

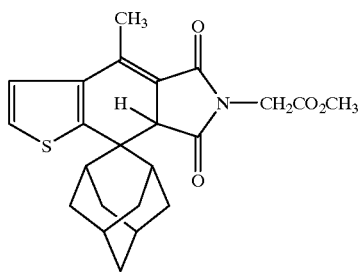

TECHNICAL PROBLEMS TO BE SOLVED BY THE INVENTION

The above fulgide or fulgimide compound is, as mentioned above, an excellent photochromic compound in that it repeats reversible color change between coloration and discoloration with good durability. The compound, however, must be used in a large amount to give a sufficiently high color density in a color-developing state. Consequently, as the compound deteriorates in proportional to the amount used, the color of the compound is not sufficiently removed in a conversion to a colorless state, with the result that the color still remains, which is a problem.

DISCLOSURE OF THE INVENTION

It is therefore an object of the present invention to provide a novel fulgimide compound which is useful as a photochromic compound.

It is another object of the present invention to provide a fulgimide compound which gives a sufficiently high color density in a color-developing state.

It is still another object of the present invention to provide a fulgimide compound which gives a sufficiently high color density for practical application even in a small amount.

A study conducted by the present inventors has revealed that the above objects of the present invention could be achieved by a fulgimide compound represented by the following general formula (I):

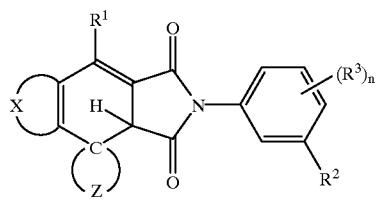
(I)

[wherein the group (a)

is a divalent aromatic hydrocarbon group or a divalent unsaturated heterocyclic group each of which may have a substituent(s);

the group (b)

is a norbornylidene group, a bicyclo[3.3.1]nonylidene group or an adamantylidene group each of which may have a substituent(s);

$R^1$ is a monovalent hydrocarbon group or a monovalent heterocyclic group each of which may have a substituent(s);

$R^2$ is an electron-attracting group;

$R^3$ is an alkyl group, an aryl group, an amino group, an alkoxy group or an electron-attracting group;

n is an integer of 0 to 4; and when n is an integer of 2 or more, a plurality of $R^3$s can be atoms or groups that are different from each other].

BEST MODE FOR CARRYING OUT THE INVENTION

In the general formula (I), the group (a) is a divalent aromatic hydrocarbon group or a divalent unsaturated heterocyclic group each of which may have a substituent(s). These groups may each have at most 5, preferably up to 3, substituents. The aromatic hydrocarbon group has 6 to 20, preferably 6 to 14 carbon atoms. Illustrative examples of the ring that forms the aromatic hydrocarbon group include a benzene ring, a naphthalene ring or a phenanthrene ring.

The unsaturated heterocyclic ring is a 5- or 6-membered hetero-monocyclic group containing 1 to 3 hetero atoms of at least one kind selected from nitrogen atom, oxygen atom and sulfur atom, or a fused heterocyclic group in which a benzene ring or a cyclohexene ring is fused to the hetero-monocyclic group. Illustrative examples of the ring that forms the heterocyclic group include a nitrogen-containing heterocyclic ring such as a pyrrole ring, a pyridine ring, a quinoline ring, an isoquinoline ring and the like; an oxygen-containing heterocyclic ring such as furan ring, benzofuran ring, pyran ring the like; and a sulfur-containing heterocyclic ring such as thiophene ring, benzothiophene ring and the like.

As mentioned above, the aromatic hydrocarbon group or unsaturated heterocyclic group represented by the group (a) may have up to 5, preferably up to 3 substituents. Illustrative examples of such substituents include a halogen atom such as fluorine, chlorine, bromine and iodine; hydroxyl group; cyano group; nitro group; amino group; carboxyl group; an alkylamino group having 1 to 4 carbon atoms such as methylamino group and diethylamino group; a lower alkyl group having 1 to 4 carbon atoms such as methyl group, ethyl group, propyl group and tert-butyl group; a halogenated lower alkyl group having 1 to 3 halogen atoms such as trifluoromethyl group, 2-chloroethyl group and the like; a lower alkoxy group having 1 to 4 carbon atoms such as methoxy group, ethoxy group and tert-butoxy group; an aryl group having 6 to 10 carbon atoms such as phenyl group, naphthyl group and toluyl group; an aryloxy group having 6 to 14 carbon atoms such as phenoxy group and 1-naphthoxy group; an aralkyl group having 7 to 15 carbon atoms such as benzyl group, phenylethyl group and phenylpropyl group; an aralkoxy group having 7 to 15 carbon atoms such as benzyloxy group and phenylpropoxy group; and an alkylthio group having 1 to 4 carbon atoms. These substituents may be the same or different when used in two or more substituents, and the position of substitution is not particularly restricted.

The group (a) is preferably a divalent aromatic hydrocarbon group or a divalent unsaturated heterocyclic group each of which may be substituted by at least one atom or group selected from the group consisting of a halogen atom, nitro group, cyano group, amino group, an alkylthio group having 1 to 4 carbon atoms, an alkyl group having 1 to 4 carbon atoms, an alkoxy group having 1 to 4 carbon atoms, an aryl group having 6 to 10 carbon atoms, and an aralkoxy group having 7 to 15 carbon atoms.

The group (a) is more preferably a 5- or 6-membered hetero-monocyclic group having one nitrogen, oxygen, or sulfur atom, which may be substituted by 1 to 3 substituents mentioned above.

The group (a) is particularly preferably a group derived from thiophene or a group derived from furan each of which may have a substituent.

In the present invention, the group (b) of the general formula (I) refers to a norbornylidene group, a bicyclo[3.3.1] nonylidene group or an adamantylidene group, each of which may have a substituent(s). The norbornylidene group is preferably a 7-norbornylidene group represented by the following formula (b-1), the bicyclo[3.3.1]nonylidene group is preferably a bicyclo[3.3.1]9-nonylidene group represented by the following formula (b-2); and the adamantylidene group is preferably a 2-adamantylidene group represented by the following formula (b-3).

(b-1)

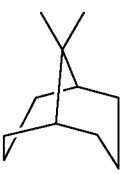

(b-2)

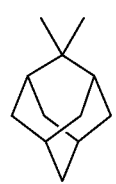

(b-3)

The above formulae (b-1), (b-2) and (b-3), which are preferred examples of the group (b), show skeletal structures of 7-nobornylidene group, bicyclo[3.3.1]9-nonylidene group and 2-adamantylidene group, each of which has no substituent.

In the 7-norbornylidene group, bicyclo[3.3.1]9-nonylidene group or 2-adamantylidene group, the hydrogen atom(s) in the formula (b-1), (b-2) or (b-3) may be substituted by a substituent or two or more substituents. When the group has a substituent, the kind, number and position thereof can be arbitrarily determined according to the purpose and application. When the group has a plurality of substituents, they may be the same or different.

As the substituent(s) for the 7-norbornylidene group, bicyclo[3.3.1]9-nonylidene group or 2-admantylidene group, there can be mentioned, for example, hydroxyl group; an alkylamino group having 1 to 4 carbon atoms such as methylamino group, diethylamino group and the like; an alkoxy group having 1 to 4 carbon atoms such as methoxy group, ethoxy group, tert-butoxy group and the like; an aralkoxy group having 7 to 15 carbon atoms such as benzyloxy group and the like; an aryloxy group having 6 to 14 carbon atoms such as phenoxy group, 1-naphthoxy group and the like; a lower alkyl group having 1 to 4 carbon atoms such as methyl group, ethyl group, tert-butyl group and the like; a halogen atom such as fluorine, chlorine, bromine and the like; cyano group; carboxyl group; an alkoxycarbonyl group having 2 to 10 carbon atoms such as ethoxycarbonyl group and the like; a halogen-substituted alkyl group having 1 to 2 carbon atoms such as trifluoromethyl group and the like; nitro group; an aryl group having 6 to 10 carbon atoms such as phenyl group, toluyl group and the like; and an aralkyl group having 7 to 9 carbon atoms such as benzyl group, phenylethyl group, phenylpropyl group and the like.

Preferred examples of these substituents are a halogen atom, hydroxyl group, an alkyl group having 1 to 4 carbon atoms, an alkoxy group having 1 to 4 carbon atoms, an alkoxycarbonyl group having 2 to 10 carbon atoms, an aralkyl group having 7 to 9 carbon atoms and an aryl group having 6 to 10 carbon atoms.

Of the above groups (b), a 2-adamantylidene group represented by the formula (b-1) is particularly preferable in that a compound having the 2-adamantylidene group shows a high color density in the color-developing state.

In the general formula (I), $R^1$ is a monovalent hydrocarbon group or a monovalent heterocyclic group, each of which may have a substituent(s).

The hydrocarbon group represented by $R^1$ may be an aliphatic, alicyclic or aromatic hydrocarbon group. Specific examples thereof are an alkyl group having 1 to 20 carbon atoms, preferably 1 to 6 carbon atoms, such as methyl group, ethyl group, propyl group and butyl group; a cycloalkyl group having 3 to 8 carbon atoms, preferably 3 to 6 carbon atoms, such as cyclopropyl group and cyclohexyl group; an aryl group having 6 to 14 carbon atoms such as phenyl group, toluyl group, xylyl group and naphthyl group; and an aralkyl group having 1 to 10 carbon atoms, preferably 1 to 4 carbon atoms, such as benzyl group, phenylethyl group, phenylpropyl group and phenylbutyl group.

The heterocyclic group represented by $R^1$ is preferably a 5- or 6-membered hetero-monocyclic group containing 1 to 3, preferably 1 to 2 hetero atoms of at least one kind selected from nitrogen atom, oxygen atom and sulfur atom, or a fused heterocyclic group in which a benzene ring is fused to the hetero-monocyclic group. Specific examples of the heterocyclic group can be saturated heterocyclic groups having saturated piperidine ring, piperazine ring, morpholine ring, pyrrolidine ring, indoline ring, coumarone ring and the like, in addition to those unsaturated heterocyclic groups that have been already mentioned with respect to the group (a).

The hydrocarbon group or heterocyclic group represented by $R^1$ may have a substituent(s). The number of substituents for hydrocarbon group or heterocyclic group is preferably at most 5, more preferably up to 3. Specific examples of the substituents are the same as those mentioned with respect to the substituents of the group (a).

Preferred examples of $R^1$ include an alkyl group having 1 to 20 carbon atoms which may be substituted by a halogen atom, an alkoxy group having 1 to 4 carbon atoms or a phenyl group; a cycloalkyl group having 3 to 8 carbon atoms which may be substituted by a halogen atom, an alkoxy group having 1 to 4 carbon atoms or a phenyl group; an aryl group having 6 to 10 carbon atoms which may be substituted by a halogen atom or an alkoxy group having 1 to 4 carbon atoms; and 5- or 6-membered hetero-monocyclic group containing 1 to 3 hetero atoms, particularly 1 hetero atom selected from nitrogen atom, oxygen atom and sulfur atom, or fused heterocyclic group in which a benzene ring is fused to the heterocyclic group, particularly hetero-monocyclic groups.

Particularly preferred as $R^1$ are an alkyl group having 1 to 6 carbon atoms, a cycloalkyl group having 3 to 6 carbon atoms, an aralkyl group having 7 to 10 carbon atoms, and an aryl group having 6 to 10 carbon atoms. Of these, an alkyl group having 1 to 6 carbon atoms and a cycloalkyl group having 3 to 6 carbon atoms are the most preferred.

In the general formula (I), $R^2$ is an electron-attracting group and there is no particular restriction as to its kind. Illustrative examples of $R^2$ include a halogen atom, a perhalogenoalkyl group, a cyano group, a substituted or unsubstituted alkoxycarbonyl group, a substituted or unsubstituted alkylcarbonyl group, a substituted or unsubstituted arylcarbonyl group, a nitro group, a sulfonyl group, a substituted or unsubstituted alkylsulfonyl group, a substituted or unsubstituted arylsulfonyl group and a substituted or unsubstituted aryloxycarbonyl groups.

Specific examples of the electron-attracting group of $R^2$ preferably include a halogen atom such as fluorine; a perhalogenoalkyl group having 1 to 4 carbon atoms such as trifluoromethyl group, pentafluoroethyl group, heptafluoropropyl group and nonafluorobutyl group; an alkoxycarbonyl group having 2 to 5 carbon atoms such as methoxycarbonyl group, ethoxycarbonyl group, propoxycarbonyl group, butoxycarbonyl group and tert-butoxycarbonyl group; an alkylcarbonyl group such as methylcarbonyl group, ethylcarbonyl group, propylcarbonyl group, butylcarbonyl group and tert-butylcarbonyl group; arylcarbonyl group having 7 to 11 carbon atoms such as benzoyl group and 1-naphthylcarbonyl group; an alkylsulfonyl group having 1 to 4 carbon atoms such as methylsulfonyl group, ethylsulfonyl group, propylsulfonyl group and tert-butylsulfonyl group; an arylsulfonyl group having 6 to 10 carbon atoms such as phenylsulfonyl group and naphthylsulfonyl group; and an aryloxycarbonyl group having 7 to 11 carbon atoms such as phenoxycarbonyl group and naphthyloxycarbonyl group.

Specific examples of the substituents for the alkoxycarbonyl group, alkylcarbonyl group, arylcarbonyl group, alkylsulfonyl group, arylsulfonyl group and aryloxycarbonyl group of these groups of $R^2$ may be the same as those mentioned with respect to the group (a). The number of the substituent may be one or more. Of these, a halogen atom and cyano group are particularly preferred. When the above groups are substituted with the halogen atom, it is preferred that all the hydrogen atoms of the alkoxy moiety, alkyl moiety or aryl moiety are substituted with the halogen atoms. As such groups, there can be mentioned perhalogenoalkoxycarbonyl group having 2 to 5 carbon atoms, such as trichloromethoxycarbonyl group, trifluoromethoxycarbonyl group, pentafluoroethoxycarbonyl group, heptafluoropropoxycarbonyl group and nonafluorobutoxycarbonyl group; perhalogenoalkylcarbonyl group having 2 to 5 carbon atoms, such as trichloromethylcarbonyl group, trifluoromethylcarbonyl group, pentafluoroethylcarbonyl group, heptafluoropropylcarbonyl group and nonafluorobutylcarbonyl group; perhalogenoarylcarbonyl group having 7 to 11 carbon atoms, such as pentafluorobenzoyl group; and so forth.

Particularly preferred as $R^2$ is a cyano group, a fluorine atom, a trifluoromethyl group or a nitro group.

In the general formula (I), the group represented by $R^3$ is an alkyl group, an aryl group, an amino group, an alkoxy group or an electron-attracting group. The number (n) of $R^3$ is 0 to 4. When the number (n) of $R^3$ is 2 or more, each of $R^3$s may be the same or different.

Illustrative examples of $R^3$ include an alkyl group having 1 to 6 carbon atoms, such as methyl group, ethyl group, propyl group, butyl group, cyclopropyl group and cyclohexyl group; an aryl group having 6 to 14 carbon atoms, such as phenyl group, toluyl group, xylyl group and naphthyl group; an alkylamino group having 1 to 5 carbon atoms or saturated heterocyclic group, such as dimethylamino group, diethylamino group, morpholino group and piperidino group; an alkoxy group having 1 to 4 carbon atoms such as methoxy group, ethoxy group and tert-butoxy group; and the same electron-attracting groups as mentioned with respect to $R^2$.

Of the above $R^3$ groups, the electron-attracting groups are preferred. Preferred electron-attracting groups are the same as those mentioned with respect to $R^2$.

When $R^3$ is an electron-attracting group, the position on the benzene ring of the general formula (I) shown in the following formula is preferred because the compound of the following formula shows a high color density in its color-developing state:

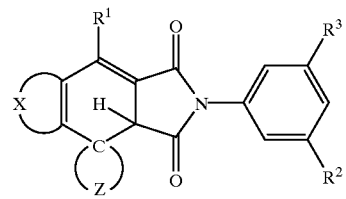

[wherein the following group (a), the following group (b),

(a)

(b)

$R^1$, and $R^2$ have the same definitions as given with respect to the general formula (I)]

While the number (n) of $R^3$ is 0 to 4, a compound having no $R^3$ (n=0) is preferred in view of the availability of raw materials.

Specific examples of the compounds of the general formula (I) which can be preferably used in the present invention are as follows.

(1) N-(3'-cyanophenyl)-6,7-dihydro-4-methyl-2-(4'-methoxyphenyl)spirobenzothiophenecarboxyimide-7,2'-tricyclo[3.3.1.13,7]decane (2) N-(3'-cyanophenyl)-6,7-dihydro-4-methyl-2-phenylspirobenzothiophenecarboxyimide-7,2'-tricyclo[3.3.1.13,7]decane (3) N-(3'-cyanophenyl)-4-cyclopropyl-6,7-dihydrospirobenzothiophenecarboxyimide-7,2'-tricyclo[3.3.1.13,7]decane (4) 6,7-dihydro-4-methyl-2-phenyl-N-(3'-trifluoromethylphenyl)spirobenzothiophenecarboxyimide-7,2'-tricyclo[3.3.1.13,7]decane (5) 6,7-dihydro-4-methyl-N-(3'-nitrophenyl) spirobenzothiophenecarboxyimide-7,2'-tricyclo[3.3.1.1³,⁷] decane (6) N-(3',5'-dicyanophenyl)-6,7-dihydro-4-methyl-2-phenylspirobenzothiophenecarboxyimide-7,2'-tricyclo [3.3.1.1³,⁷]decane (7) N-(3'-fluorophenyl)-6,7-dihydro-4-methyl-2-phenylspirobenzothiophenecarboxyimide-7,2'-tricyclo [3.3.1.1³,⁷]decane (8) N-(3'-acetylphenyl)-6,7-dihydro-4-methyl-2-phenylspirobenzothiophenecarboxyimide-7,2'-tricyclo [3.3.1.1³,⁷]decane (9) N-(3'-benzoylphenyl)-6,7-dihydro-4-methyl-2-phenylspirobenzothiophenecarboxyimide-7,2'-tricyclo [3.3.1.1³,⁷]decane

(10) 6,7-dihydro-4-methyl-N-(3'-methylsulfonylphenyl)-2-phenylspirobenzothiophenecarboxyimide-7,2'-tricyclo [3.3.1.1³,⁷]decane

(11) 6,7-dihydro-4-methyl-2-phenyl-N-(3'-phenylsulfonylphenyl)spirobenzothiophenecarboxyimide-7, 2'-tricyclo[3.3.1.1³,⁷]decane The fulgimide compound represented by the general formula (I) according to the present invention exists generally as a pale yellow or colorless solid at normal temperature and can be identified as such, generally by the following analytical means (A) to (C).

(A) By measuring proton nuclear magnetic resonance spectrum ($^1$H-NMR), the kind and number of the protons present in the molecule can be determined. Specifically, there appear a peak based on the aromatic protons near δ7 to 8 ppm, a broad peak based on the protons derived from the norbornylidene group, bicyclo[3.3.1]nonylidene group or adamantylidene group near δ1.2 to 2.5 ppm, and a peak based on the alkyl group near δ1.2 to 4.0 ppm when $R^1$ is an alkyl group. By comparing the δ peak intensities of these peaks relatively, the number of protons of each bonding group can be obtained.

(B) By elemental analysis, the weight percentages of carbon, hydrogen, nitrogen, sulfur and halogen atoms can be determined. The weight percentage of oxygen can be calculated by subtracting the total of the weight percentages of these elements from 100. Consequently, the composition of the corresponding product can be determined.

(C) By measuring $^{13}$C-nuclear magnetic resonance spectrum ($^{13}$C-NMR), the kind of the carbons present in the molecule can be ascertained. There appear a peak derived from the carbons of the norbornylidene group, bicyclo [3.3.1]nonylidene group or adamantylidene group near δ27 to 52 ppm, a peak based on an alkyl group near δ15 to 35 ppm when $R^1$ is an alkyl group, a peak based on the carbons of the aromatic hydrocarbon group or unsaturated heterocyclic group near δ110 to 150 ppm, and a peak based on the carbon of the

near δ160 to 170 ppm.

The fulgimide compound of the general formula (I) according to the present invention can be produced by any production process, and there is no restriction as to the type of the production process. A preferable and typical process will be described below, while the present invention is not limited thereto.

There can be mentioned a process which comprises reacting an acid anhydride represented by the following general formula (II):

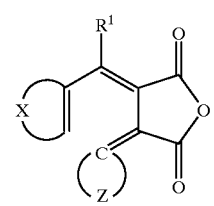

(II)

[wherein the following group (a), the following group (b)

(a)

(b)

and $R^1$ have the same definitions as given with regard to the general formula (I)], with an amine compound represented by the following general formula (III):

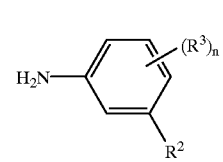

(III)

[wherein $R^2$, $R^3$ and n have the same definitions as given with regard to the general formula (I)] and then cyclizing the reaction product.

The reaction of the acid anhydride of the formula (II) with the amine compound of the formula (III) is carried out preferably in a solvent. The solvent may be an aprotic polar solvent such as tetrahydrofuran, 1,4-dioxane or the like.

In the reaction of the acid anhydride of the formula (II) with the amine compound of the formula (III), the amount ratio of the acid anhydride to the amine compound can be selected from a wide range, but is generally 1:10 to 10:1, preferably 1:5 to 5:1 in terms of molar ratio.

The above reaction is carried out generally at 25 to 160° C. for 1 to 24 hours. After the completion of the reaction, the solvent is removed, and the resulting product is dehydrated with dicyclohexylcarbodiimide (DCC). Thereafter, the resulting compound is subjected to cyclization under the following conditions to obtain a compound (I) of the present invention.

The cyclization subsequent to the reaction of the acid anhydride with the above amine compound is preferably carried out, for example, by heating the resulting compound to a temperature of 160–220° C., or by carrying out this heating with ultraviolet irradiation, or by bringing it into contact with a Lewis acid catalyst. Known compounds such as $SnCl_4$, $TiCl_4$, $SbCl_5$ and $AlCl_3$ can be used as the Lewis acid catalyst without any restriction. Although there is also no particular restriction as to the amount of the Lewis acid catalyst used, the Lewis acid catalyst, in general, is used preferably in an amount of 0.001 to 1 mole per mole of the compound to be cyclized.

In the above production process, the acid anhydride of the general formula (II) used as a starting material can be produced by the following process, for example.

That is, the acid anhydride of the formula (II) can be obtained by subjecting a carbonyl compound represented by the following general formula (IIa):

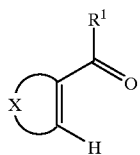

(IIa)

[wherein the following group (a)

(a)

and $R^1$ have the same definitions as given with regard to the general formula (I)]
and a succinic diester derivative represented by the following general formula (IIb):

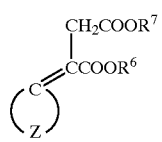

(IIb)

[wherein the following group (b)

(b)

has the same definition as given with regard to the general formula (I), and $R^6$ and $R^7$ may be the same or different and are each an alkyl group having 1 to 6 carbon atoms]
to a condensation reaction, and then conducting a treatment mentioned later.

In the condensation reaction, the amount ratio of the carbonyl compound of the general formula (IIa) to the succinic diester derivative of the general formula (IIb) can vary over a wide range, but is generally 1:10 to 10:1, preferably 1:5 to 5:1 in terms of molar ratio. The reaction is carried out generally at 0 to 110° C., preferably at 10 to 100° C. It is appropriate to conduct the reaction in the presence of a solvent, and the solvent is desirably an aprotic solvent such as benzene, diethyl ether, toluene, tetrahydrofuran or the like.

The condensation reaction is carried out generally in the presence of a condensation agent such as sodium hydride, tert-butoxide, sodium ethylate or the like. The condensation agent is used in an amount of usually 0.1 to 10 moles per mole of the carbonyl compound of the general formula (IIa).

After the completion of the condensation reaction, the resulting dicarboxylic acid diester is converted to a free dicarboxylic acid. This reaction is carried out under the conditions of hydrolysis in the presence of a base, which are generally known per se. For example, the reaction is conducted at 0 to 80° C. using an ethanolic aqueous solution of 10% sodium hydroxide.

The thus-obtained dicarboxylic acid is converted to an acid anhydride by a method known per se to obtain an acid anhydride of the general formula (II). The acid anhydride is obtained, for example, by using a well known reagent such as acetic anhydride, acetyl chloride or the like.

The fulgimide compound of the general formula (I) according to the present invention has a photochromic action of excellent durability by itself. The durability of the photochromic action of the fulgimide compound is further enhanced when it is used in combination with an ultraviolet stabilizer.

The fulgimide compound of the general formula (I) according to the present invention is well soluble in regular organic solvents such as toluene, chloroform and tetrahydrofuran. When the compound of the general formula (I) is dissolved in such a solvent, the solution is nearly colorless and transparent. The solution develops a color when irradiated with sunlight or ultraviolet rays, and it rapidly returns to its original colorless state when the light is shut off. Thus, the solution shows an excellent reversible photochromic action. Such a photochromic fluid can be used in applications such as decoration and the like.

The fulgimide compound of the general formula (I) shows an excellent photochromic action in a polymeric material as well. Such a polymeric material can be advantageously used in applications such as photochromic glass, photochromic lens and the like.

As a polymer in which the fulgimide compound of the general formula (I) is dispersed, there can be used a thermoplastic resin and a thermosetting resin. The thermoplastic resin can be any thermoplastic resins as long as it can uniformly disperse the fulgimide compound of the general formula (I) therein. There can be preferably used, for example, polymers such as polymethyl acrylate, polyethyl acrylate, polymethyl methacrylate, polyethyl methacrylate, polystyrene, polyacrylonitrile, polyvinyl alcohol, polyacrylamide, poly(2-hydroxyethyl methacrylate), polydimethylsiloxane, polycarbonate, poly(allyl diglycol carbonate) and the like; and copolymers obtained by copolymerizing monomers that constitute the above polymers with each other or with other monomer(s).

As a thermosetting resin in which the fulgimide compound of the general formula (I) is dispersed, known thermosetting resins can be used without restriction. Illustrative examples of the thermosetting resin include an urethane resin obtained by subjecting a polyfunctional isocyanate and either a polyfunctional mercapto compound or a polyfunctional hydroxy compound to addition polymerization, an epoxy resin obtained by curing a polyfunctional epoxy compound, and a resin obtained by curing a polyfunctional radical-polymerizable monomer.

The fulgimide compound of the general formula (I) can be preferably dispersed in a polymer by polymerizing a mixture of the fulgimide compound of the general formula (I) and a polymerizable monomer. When the polymer is a thermoplastic resin, the fulgimide compound can be dispersed by melt-kneading the thermoplastic resin and the fulgimide compound of the general formula (I) at a temperature not lower than the melting point of the thermoplastic resin.

When a photochromic composition is prepared by mixing the fulgimide compound of the general formula (I) with a polymerizable monomer, the amount of the fulgimide compound is generally 0.001 to 10 parts by weight, preferably 0.01 to 1 part by weight, based on 100 parts by weight of the polymerizable monomer.

The polymerizable monomer to be mixed with the fulgimide compound of the general formula (I) is preferably a radical-polymerizable monomer in order to avoid the reduction in photochromic property that is caused by the polymerizable group remaining after polymerization. The polymerizable group of the radical-polymerizable monomer may be a vinyl group, an allyl group, an acryloyl group, a methacryloyl group, and the like. An acryloyl group or methacryloyl group is particularly preferably used in order to obtain an excellent photochromic property.

Specific examples of the polymerizable monomer that can be preferably used in the present invention are as follows. The polyfunctional radical-polymerizable monomer having a vinyl group or allyl group may be polyvalent allyl compounds such as diallyl phthalate, diallyl terephthalate, diallyl isophthalate, diallyl tartarate, diallyl epoxysuccinate, diallyl fumarate, diallyl chlorendate, diallyl hexaphtalate, diallyl carbonate, allyl diglycol carbonate, trimethylolpropane triallyl carbonate and the like; esters of polyvalent thioacrylic acid or polyvalent thiomethacrylic acid, such as 1,2-bis(methacryloylthio)ethane, bis(2-acryloylthioethyl)ether, 1,4-bis(methacryloylthiomethyl)benzene and the like; and divinylbenzene and the like.

The polyfunctional radical-polymerizable monomer having an acryloyl group or methacryloyl group (simply abbreviated as "polyfunctional (meth)acrylate monomer" hereinafter) may be monomers represented by the following general formula (IV):

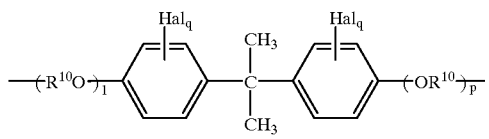

[wherein $R^8$ is a hydrogen atom or a methyl group, $R^9$ is an alkylene group having 1 to 4 carbon atoms or a group represented by the following formula:

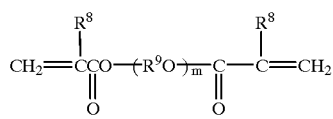

(wherein $R^{10}$ is an alkylene group having 1 to 4 carbon atoms,

Hal is a halogen atom;

l and p are each an integer of 0 to 10, and q indicates the number of the halogen atoms substituted and is an integer of 0 to 4), and m is an integer of 1 to 10], and monomers represented by the following general formula (V):

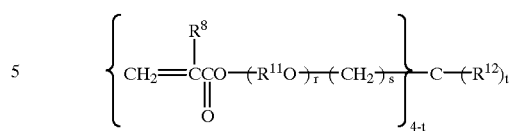

(wherein $R^8$ is a hydrogen atom or a methyl group, $R^{11}$ is an ethylene group or propylene group, r is an integer of 0 to 10, s is 0 or 1, t is an integer of 0 to 2, and $R^{12}$ is a hydrogen atom, a hydroxymethyl group or a lower alkyl group such as methyl group, ethyl group or the like). In the present invention, the term "(meth)acrylate" is a general term for methacrylate compound and acrylate compound.

The polyfunctional radical-polymerizable monomer may be mixed, as required, with a monofunctional (meth)acrylate monomer to obtain a copolymer. The monofunctional (meth)acrylate monomer that can be preferably used may be monomers represented by the following general formula (VI):

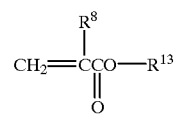

(wherein $R^8$ is a hydrogen atom or a methyl group; and $R^{13}$ is an alkyl group having 1 to 4 carbon atoms that may be substituted by a hydroxyl group, an aryl group having 6 to 10 carbon atoms that may be substituted by a halogen atom, or an aralkyl group having 7 to 10 carbon atoms that may be substituted by a halogen atom).

The alkylene group having 1 to 4 carbon atoms represented by $R^9$ or $R^{10}$ in the formula (IV) may be methylene group, ethylene group, propylene group, isopropylene group, butylene group, isobutylene group, trimethylene group and tetramethylene group. The alkyl group having 1 to 4 carbon atoms, which is represented by $R^{13}$ of the formula (VI) and may be substituted by a hydroxyl group, may be a methyl group, ethyl group, propyl group, butyl group, hydroxyethyl group and hydroxypropyl group; the aryl group having 6 to 10 carbon atoms that may be substituted by a halogen atom may be a phenyl group, naphthyl group, chlorophenyl group, dichlorophenyl group, trichlorophenyl group, chloronaphthyl group and trichloronaphthyl group; and the aralkyl group having 7 to 10 carbon atoms that may be substituted by a halogen atom may be a benzyl group, phenethyl group, chlorobenzyl group, bromobenzyl group, trichlorobenzyl group and tribromobenzyl group.

Specific examples of the compounds that can be preferably used as the polyfunctional (meth)acrylate monomer represented by the general formula (IV) or (V) include ethylene glycol di(meth)acrylate, diethylene glycol di(meth)acrylate, triethylene glycol di(meth)acrylate, tetraethylene glycol di(meth)acrylate, polyethylene glycol di(meth)acrylate, propylene glycol di(meth)acrylate, dipropylene glycol di(meth)acrylate, tripropylene glycol di(meth)acrylate, tetrapropylene glycol di(meth)acrylate, polypropylene glycol di(meth)acrylate, polybutylene glycol di(meth)acrylate, 1,6-hexanediol di(meth)acrylate, neopentyl glycol di(meth)acrylate, acrylic acid or methacrylic acid ester of 2,2'-bis(4-methacryloyloxyethoxyphenyl)propane, acrylic acid or methacrylic acid ester of 2,2'-bis(4- methacryloyloxy•polyethoxyphenyl)propane, acrylic acid or methacrylic acid ester of 2,2'-bis(4-methacryloyloxypropoxyphenyl)propane, acrylic acid or methacrylic acid ester of 2,2'-bis(4-methacryloyloxy•polypropoxyphenyl)propane, acrylic acid or methacrylic acid ester of 2,2'-bis[(3,5-dibromo-4-methacryloyloxyethoxyphenyl]propane, trimethylolpropane tri(meth)acrylate and pentaerythritol tetra(meth)acrylate. These polyfunctional (meth)acrylate monomers may be used alone or in combination of two or more.

Specific examples of the compounds that can be preferably used as the monofunctional (meth)acrylate monomer represented by the general formula (VI) include methyl (meth)acrylate, ethyl (meth)acrylate, butyl (meth)acrylate, benzyl (meth)acrylate, phenyl (meth)acrylate, 2-hydroxyethyl (meth)acrylate and tribromophenyl (meth) acrylate. These monofunctional (meth)acrylate monomers may be used alone or in combination of two or more.

When α-methylstyrene dimer is added to the photochromic composition containing the compound of the general formula (I) and the polymerizable monomer, the moldability at the time of curing can be improved and a polymer can be obtained in a higher yield. The moldability can be further improved by adding a monofunctional radical-polymerizable monomer capable of controlling polymerization, such as α-methylstyrene. Therefore, the photochromic composition preferably comprises 0.1 to 2 parts by weight of α-methylstyrene dimer, 0 to 15 parts by weight of α-methylstyrene and 0.001 to 10 parts by weight of a fulgimide compound of the general formula (I), based on 100 parts by weight of a polymerizable monomer.

It is preferred to add a polymerizable monomer having molecules each having at least one epoxy group (simply abbreviated as "epoxymonomer" hereinafter) to the photochromic composition because the durability of the fulgimide compound of the general formula (I) can be improved.

A compound comprising molecules each having at least one epoxy group and a radical-polymerizable group can be preferably used as the epoxy monomer. The radical-polymerizable group may be a vinyl group, allyl group, acryloyl group and methacryloyl group, and an acryloyl group or methacryloyl group is preferred to obtain an excellent photochromic property. An epoxy monomer that can be preferably used in the present invention can be represented by the following general formula (VII):

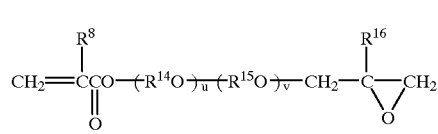

(VII)

(wherein $R^8$ and $R^{16}$ are each a hydrogen atom or a methyl group independently; $R^{14}$ and $R^{15}$ may be the same or different and are either an alkylene group having 1 to 4 carbon atoms which may be substituted by a hydroxyl group or a group represented by the following group:

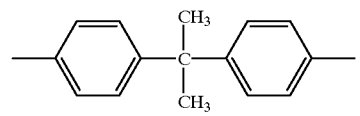

and u and v are each 0 or 1 independently).

In the above formula, the alkylene group represented by $R^{14}$ or $R^{15}$ may be a methylene group, ethylene group, propylene group, butylene group, trimethylene group and tetramethylene group. These groups may be substituted by a hydroxyl group.

Specific examples of the compounds that can be preferably used as the epoxy monomer in the present invention include methacrylate compounds and acrylate compounds such as glycidyl (meth)acrylate, β-methylglycidyl (meth) acrylate, bisphenol A-monoglycidyl ether-(meth)acrylate, 4-glycidyloxybutyl (meth)acrylate, 3-(glycidyl-2-oxyethoxy)-2-hydroxypropyl (meth)acrylate, 3-(glycidyloxy-1-isopropyloxy)-2-hydroxypropyl (meth) acrylate, 3-(glycidyloxy-2-hydroxypropyloxy)-2-hydroxypropyl(meth)acrylate and the like. Of these compounds, glycidyl (meth)acrylate is preferred in order to improve the durability of photochromic action.

It is preferred to use the epoxy monomer in an amount of generally 1 to 30 parts by weight, preferably 1 to 10 parts by weight, based on 100 parts by weight of the polymerizable monomer, preferably the radical-polymerizable monomer, more preferably the polyfunctional and/or monofunctional (meth)acrylate monomer in order to improve the durability of the photochromic action of the fulgimide compound of the general formula (I) and to prevent the deterioration of heat resistance of the compound.

The fulgimide compound of the general formula (I) is a compound capable of developing a color between violet and blue. However, a photochromic composition developing a medium color such as gray, amber or brown that is preferably used for ordinary photochromic lens can be obtained by combining the fulgimide compound with other known photochromic compounds. The other known photochromic compounds used in combination with the fulgimide compound of the present invention are preferably a spirooxazine compound or/and a chromene compound.

The chromene compound has a chromene skeleton, and known compounds having a photochromic action can be used as the chromene compound without any restriction. For example, a chromene compound represented by the following general formula (VIII) can be preferably used.

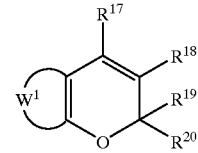

(VIII)

[wherein
$R^{17}$, $R^{18}$, $R^{19}$ and $R^{20}$ may be the same or different and are each a hydrogen atom, an alkyl group, a substituted or unsubstituted aryl group, a substituted amino group, an unsaturated heterocyclic group or a saturated heterocyclic group;

$R^{19}$ and $R^{20}$ may together form a ring; and the following group:

is a divalent aromatic hydrocarbon group or a divalent unsaturated heterocyclic group, each of which may have a substituent(s)].

In the general formula (VIII), the alkyl group represented by $R^{17}$, $R^{18}$, $R^{19}$ or $R^{20}$ may be an alkyl group having 1 to 4 carbon atoms such as methyl group, ethyl group, or propyl group. The aryl group may be an aryl group having 6 to 10 carbon atoms such as phenyl group or naphthyl group. The substituted aryl group may be a 4-methoxyphenyl group, 3-fluoro-4-methoxyphenyl group, and the like. The substituted amino group may be an amino group in which at least one of the hydrogen atoms is substituted by an alkyl group or aryl group such as methylamino group, ethylamino group, dimethylamino group, phenylamino group, or naphthylamino group. The unsaturated heterocyclic group may be either a monovalent group derived from a 5- or 6-membered ring containing 1 or 2 hetero atoms selected from nitrogen atom, oxygen atom and sulfur atom, such as pyrrole ring, pyridine ring, indoline ring, furan ring, benzofuran ring, thiophene ring or benzothiophene ring, or a monovalent group derived from a fused ring between the above monovalent group and either a benzene ring or a cyclohexane ring, such as benzothiophene ring, tetrahydrobenzothiophene ring, benzofuran ring or tetrahydrobenzofuran ring. The saturated heterocyclic group may be a monovalent group derived from a 5- to 6-membered ring containing 1 or 2 hetero atoms selected from nitrogen atom, oxygen atom and sulfur atom, such as pyrrolidine ring, imidazolidine ring, piperidine ring, piperazine ring, or morpholine ring.

In the general formula (VIII), the ring formed by $R^{19}$ and $R^{20}$ together may be a norbornylidene group, bicyclo[3.3.1]9-nonylidene group, and the like.

Also in the general formula (VIII), the divalent aromatic hydrocarbon group or unsaturated heterocyclic group represented by the following formula:

may be a divalent group derived from a benzene ring or from a fused ring formed of 2 to 3 benzene rings. The divalent unsaturated heterocyclic group represented by the same formula may be either a divalent group derived from a 5- to 7-membered ring containing 1 or 2 hetero atoms selected from nitrogen atoms, oxygen atoms and sulfur atoms, or one derived from a fused ring between the 5- to 7-membered ring and either a benzene ring or a cyclohexane ring.

Specific examples of the divalent hydrocarbon group include a group having 6 to 14 carbon atoms which is derived from a benzene ring, naphthalene ring, phenanthrene ring, anthracene ring, or the like. Specific examples of the divalent unsaturated heterocyclic group include a group having 4 to 9 carbon atoms which is derived from a pyridine ring, quinoline ring, isoquinoline ring, pyrrole ring, indole ring, furan ring, benzofuran ring, tetrahydrobenzofuran ring, thiophene ring, benzothiophene ring or tetrahydrobenzothiophene ring. Although there is no restriction as to the substituents for these groups, such substituents may be a halogen atom such as fluorine, chlorine, bromine or iodine; an alkyl group having 1 to 20 carbon atoms such as methyl group or ethyl group; an alkoxy group having 1 to 20 carbon atoms such as methoxy group or ethoxy group; aryl group having 6 to 10 carbon atoms such as phenyl group, tolyl group or xylyl group; an alkoxyaryl group having 7 to 14 carbon atoms (aryl group having 6 to 10 carbon atoms that is substituted by an alkoxy group having 1 to 4 carbon atoms); amino group; nitro group; cyano group; and a monovalent saturated heterocyclic group such as a pyrrolidine ring, imidazolidine ring, piperidine ring, piperazine ring, or morpholine ring.

In the present invention, the chromene compound is particularly preferably a compound of the general formula (VIII) wherein $R^{17}$ and $R^{18}$ are each a hydrogen atom; $R^{19}$ and $R^{20}$ may be the same or different and are each an alkyl group having 1 to 4 carbon atoms, an aryl group having 6 to 10 carbon atoms, or an unsaturated heterocyclic group, or they may together form a bicyclo[3.3.1]9-nonylidene group or norbornylidene group; and the group:

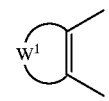

is a group that is derived from a naphthalene ring and may be substituted by an alkoxy group having 1 to 20 carbon atoms or by a monovalent saturated heterocyclic group.

Specific examples of the chromene compound that can be preferably used in the present invention are as follows.

(1) spiro(norbornane-2,2'-(2H)benzo(h)chromene)
(2) spiro(bicyclo[3.3.1]nonane-9,2'-(2H)benzo(h)chromene)
(3) 7'-methoxyspiro(bicyclo(3.3.1)nonane-9,2'-(2H)benzo(h)chromene)
(4) 7'-methoxyspiro(norbornane-2,2'-(2H)benzo(h)chromene)
(5) 2,2-dimethyl-7-octoxy(2H)benzo(f)chromene
(6) 2,2-(2'-difuryl)(2H)benzo(f)chromene
(7) 2,2-(phenyl-2'-furyl)(2H)benzo(f)chromene
(8) 9-morpholino-2,2-diphenyl(2H)benzo(f)chromene
(9) 9-morpholino-2,2-bis(3-fluoro-4-methoxyphenyl)(2H)benzo(f)chromene
(10) 2,2-((2'-(3'-fluoronaphthyl))-2'-thienyl)(2H)benzo(f)chromene The spirooxazine compound that can be used in combination with the fulgimide compound of the general formula (I) has a spirooxazine skeleton. Known compounds having a photochromic action can be used as the spirooxazine compound without any restriction. For example, a spirooxazine compound represented by the following general formula (IX) can be preferably used.

(IX)

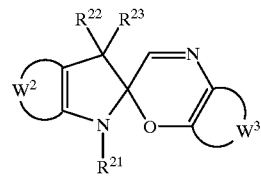

[wherein $R^{21}$, $R^{22}$ and $R^{23}$ may be the same or different and are each an alkyl group, a cycloalkyl group, an alkyloxyalkyl group, an alkoxycarbonyl group, an alkoxycarbonylalkyl group, an aryl group, an aralkyl group, an alkylthioalkyl group, an acyl group or an acyloxy group;

$R^{22}$ and $R^{23}$ may together form a ring;

$R^{21}$, $R^{22}$ and $R^{23}$ may each have a substituent;

the group represented by:

is a divalent aromatic hydrocarbon group or a divalent unsaturated heterocyclic group each of which may be substituted;

and the group represented by:

is a divalent aromatic hydrocarbon group or a divalent unsaturated heterocyclic group each of which may be substituted].

In the general formula (IX), the alkyl group represented by $R^{21}$, $R^{22}$ or $R^{23}$ may be an alkyl group having 1 to 5 carbon atoms, such as methyl group, ethyl group, isopropyl group, n-propyl group, n-butyl group, isobutyl group, or neopentyl group. The aryl group may be an aryl group having 6 to 10 carbon atoms, such as phenyl group or naphthyl group. The cycloalkyl group may be a cycloalkyl group having 3 to 8 carbon atoms, such as cyclopropyl group, cyclobutyl group, or cyclohexyl group. The alkyloxyalkyl group may be an alkyloxyalkyl group having 2 to 10 carbon atoms, such as methyloxymethyl group, methyloxyethyl group, or ethyloxymethyl group. The alkoxycarbonyl group may be an alkoxycarbonyl group having 2 to 10 carbon atoms, such as methoxycarbonyl group or ethoxycarbonyl group. The alkoxycarbonylalkyl group may be an alkoxycarbonylalkyl group having 3 to 15 carbon atoms, such as methoxycarbonylmethyl group, ethoxycarbonylmethyl group, or methoxycarbonylethyl group. The aralkyl group may be an aralkyl group having 7 to 20 carbon atoms, such as benzyl group, phenylethyl group, naphtylmethyl group or the like. The alkylthioalkyl group may be an alkylthioalkyl group having 2 to 10 carbon atoms, such as methylthiomethyl group, methylthioethyl group, or ethylthiomethyl group. The acyl group may be an acyl group having 2 to 10 carbon atoms, such as acetyl group or ethylcarbonyl group. The alkylcarbonyloxy group may be an alkylcarbonyloxy group having 2 to 10 carbon atoms, such as methylcarbonyloxy group or ethylcarbonyloxy group.

The substituents for the above groups may be a halogen atom, nitro group, cyano group, heterocyclic group, and the like.

In the general formula (IX), the divalent aromatic hydrocarbon group or the divalent unsaturated heterocyclic group each of which may be substituted, represented by:

is the same as those mentioned with respect to the general formula (VIII).

Also in the general formula (IX), the divalent aromatic hydrocarbon group or the divalent unsaturated heterocyclic group each of which may be substituted, represented by:

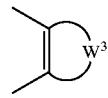

is the same as those mentioned with respect to the general formula (VIII).

The substituents for these groups may be selected from those listed as the substituents for the groups in the general formula (VIII). Particularly preferred is a group represented by —$NR^{24}R^{25}$ (wherein $R^{24}$ and $R^{25}$ are each an alkyl group, an alkoxy group or an aryl group, each of which may be substituted and they may bond to each other for cyclization to form a nitrogen-containing heterocyclic ring.

In the spirooxazine compound of the general formula (IX), $R^{21}$ is preferably either an alkyl group or an alkoxycarbonylakyl group; $R^{22}$ and $R^{23}$ are each an alkyl group or form together a ring (a cycloalkyl group); and the group represented by:

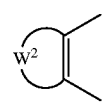

is an aromatic hydrocarbon group which may be partially or wholly substituted. Particularly, it is preferable that the aromatic hydrocarbon group that may be substituted is an aromatic hydrocarbon group that has been partially or wholly substituted by an alkyl group(s) or a halogen atom, particularly a fluorine atom; and the group represented by:

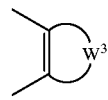

is a substituted or unsubstituted aromatic hydrocarbon group, particularly an amino group-substituted naphthalene ring.

Specific examples of the spirooxazine compounds that can be preferably used in the present invention are as follows.

(1) 1',5'-dimethyl-6'-fluoro-6"-morpholinodispiro (cyclohexane-1,3'-(3H)indole-2'-(2H),3"-(3H)naphtho(3,2-a)(1,4)oxazine (2) 6'-fluoro-1'-methoxycarbonylethyl-8"-methoxy-6"-piperidinodispiro(cyclohexane-1,3'-(3H)indole-2'-(2H), 3"-(3H)naphtho(3,2-a)(1,4)oxazine (3) 1'-(2-(dioxane-2-yl)ethyl)-6'-fluoro-6"-(4-methylpiperazino)dispiro(cyclohexane-1,3'-(3H)indole-2'-(2H),3"-(3H)naphtho(3,2-a)(1,4)oxazine (4) 5',7'-difluoro-1'-methyl-6"-morpholinodispiro (cyclohexane-1,3'-(3H)indole-2'-(2H),3"-(3H)naphtho(3,2-a)(1,4)oxazine (5) 1'-isobutyl-5'-methyl-6'-fluoro-6"-morpholinodispiro (cyclohexane-1,3'-(3H)indole-2'-(2H),3"-(3H)naphtho(3,2-a)(1,4)oxazine In the photochromic composition of the present invention, the fulgimide compound of the general formula (I), the chromene compound of the general formula (VIII) and/or the spirooxazine compound of the general formula (IX) may be used alone or as a mixture of two or more. There is no restriction as to the mixing ratio of these photochromic compounds, and the mixing ratio can be appropriately determined in consideration of the properties of the individual photochromic compounds used. In general, the fulgimide compound of the general formula (I), and the chromene compound of the general formula (VIII) and/or the spirooxazine compound of the general formula (IX) are each contained preferably in an amount of generally 0.001 to 10 parts by weight, more preferably 0.01 to 0.2 part by weight, based on 100 parts by weight of the polymerizable monomer.

When the above photochromic compounds are used in combination, since each of them has different durability, the resulting photochromic cured product may have so called "color shift" which means that a developed color before and after use causes shift in a tone when used over a long period of time. Such a problem, however, can be prevented by appropriately selecting the kind and mixing ratio of the individual compound used. For example, the following composition can be recommended.

A composition which can be obtained by mixing:

[1] 100 parts by weight of a polymerizable monomer comprising:

(A) 100 parts by weight of a radical-polymerizable monomer represented by the general formula (IV), (V) or (VI), and (B) 0 to 30 parts by weight, preferably 1 to 30 parts by weight, of an epoxy monomer represented by the general formula (VII), with

[2] the following photochromic compounds comprising:

(C) 0.01 to 0.05 part by weight, preferably 0.01 to 0.03 part by weight, of the fulgimide compound represented by the general formula (I), (D) 0.01 to 0.2 part by weight, preferably 0.01 to 0.1 part by weight, of the chromene compound represented by the general formula (VIII), (E) 0.03 to 0.1 part by weight, preferably 0.03 to 0.06 part by weight, of a spirooxazine compound represented by the general formula (IX), the weight ratio of the amount of (C) to the amount of (E), [(C)/(E)], being 1 or less.

The "color shift" as mentioned above can also be prevented by adding an ultraviolet stabilizer. Known ultraviolet stabilizers used in various plastics can be used as the ultraviolet stabilizer without any restriction. Of various ultraviolet stabilizers, a benzotriazole-based ultraviolet stabilizer, a light extinguisher for oxygen in the singlet state and a hindered amine light stabilizer (including a light stabilizer comprising molecules each having a hindered amine structure and a hindered phenol structure) are particularly preferred in view of the improvement of the durability of photochromic compound.

Known compounds having a benzotriazole skeleton and an ultraviolet absorbability can be used without any restriction.

For example, a benzotriazole-based ultraviolet absorber represented by the following general formula (X) can be preferably used.

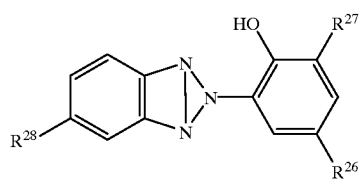

(X)

(wherein $R^{26}$ and $R^{27}$ may be the same or different and are each a hydrogen atom, an alkyl group, an aryl group or an aralkyl group; and $R^{28}$ is a hydrogen atom or a chlorine atom).

In the general formula (X), the alkyl group represented by $R^{26}$ and $R^{27}$ may be an alkyl group having 1 to 10 carbon atoms such as a methyl group, butyl group, sec-butyl group, or tert-butyl group; the aryl group may be an aryl group having 6 to 20 carbon atoms such as a phenyl group, butylphenyl group, sec-butylphenyl group, or tert-butylphenyl group; the aralkyl group may be an aralkyl group having 7 to 20 carbon atoms such as a benzyl group or phenylethyl group.

Preferred as the benzotriazole-based ultraviolet absorber is a compound of the general formula (X) wherein $R^{26}$ and $R^{27}$ are the same or different and are each an alkyl group having 1 to 5 carbon atoms, particularly a methyl group, a tert-butyl group or a tert-amyl group; or an aryl group having 6 to 15 carbon atoms, particularly a methylphenyl group, a tert-butylphenyl group or a tert-octylphenyl group; or an aralkyl group having 7 to 15 carbon atoms, particularly a benzyl group or an α,α-dimethylbenzyl group.

Specific examples of the benzotriazole-based ultraviolet absorber that can be preferably used in the present invention are as follows.

(1) 2-(5-methyl-2-hydroxyphenyl)benzotriazole (trade name: Tinuvin P, a product of Ciba-Geigy Japan Limited)

(2) 2-[2-hydroxy-3,5-bis(α,α-dimethylbenzyl)phenyl]-2H-benzotriazole (trade name: Tinuvin 234, a product of Ciba-Geigy Japan Limited)

(3) 2-(3,5-di-tert-butyl-2-hydroxyphenyl)benzotriazole (trade name: Tinuvin 320, a product of Ciba-Geigy Japan Limited)

(4) 2-(3-tert-butyl-5-methyl-2-hydroxyphenyl)-5-chlorobenzotriazole (trade name: Tinuvin 326, a product of Ciba-Geigy Japan Limited)

(5) 2-(3,5-di-tert-butyl-2-hydroxyphenyl)-5-chlorobenzotriazole (trade name: Tinuvin 327, a product of Ciba-Geigy Japan Limited)

(6) 2-(3,5-di-tert-amyl-2-hydroxyphenyl)benzotriazole (trade name: Tinuvin 328, a product of Ciba-Geigy Japan Limited)

(7) 2-(2'-hydroxy-5'-tert-octylphenyl)benzotriazole (trade name: Tinuvin 329, a product of Ciba-Geigy Japan Limited)

The amount of the ultraviolet absorber added is preferably 0.005 to 0.1 part by weight, more preferably 0.01 to 0.05 part by weight, based on 100 parts by weight of the polymerizable monomer.

The light extinguisher for oxygen in the singlet state as an ultraviolet stabilizer may be a complex between $Ni^{2+}$ and an organic ligand, cobalt (III)-tris-di-n-butyldithiocarbamate, iron (III)-diisopropyldithiocarbamate, cobalt (II)-diisopropyldithiocarbamate, and the like. Of these light extinguishers for oxygen in the singlet state, a complex between $Ni^{2+}$ and organic ligand is particularly preferred. Specific examples of such a complex include the following complexes u-1 to u-4.

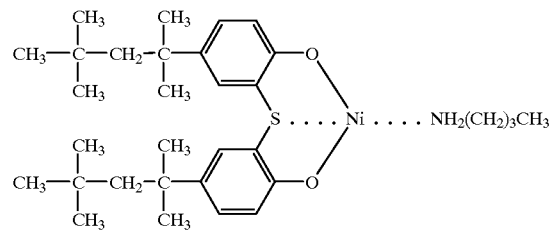

[2,2'-thiobis(4-(1,1,3,3-tetramethylbutyl)phenolate) butylamine]nickel

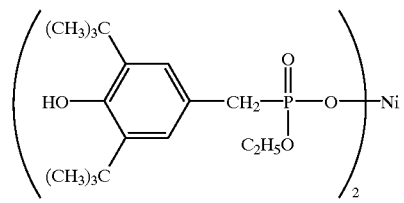

nickel-bis[o-ethyl(3,5-di-tert-butyl-4-hydroxybenzyl)] phosphonate

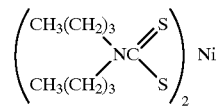

nickel-dibutyldithiocarbamate

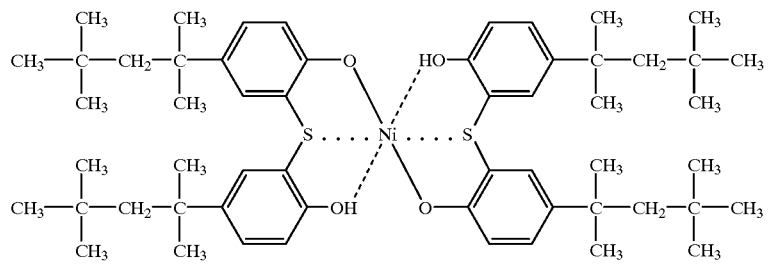

bis[2,2'-thiobis-4-(1,1,3,3-tetramethylbutyl)phenolate] nickel

In addition to these, there can be mentioned Ni complexes provided by Ferro Corporation under the trade names of UV-Chek AM105, UV-Chek AM126 and UV-Chek AM205.

Specific examples of the hindered amine light stabilizer that can be preferably used as an ultraviolet stabilizer include the following compounds u-5 to u-12.

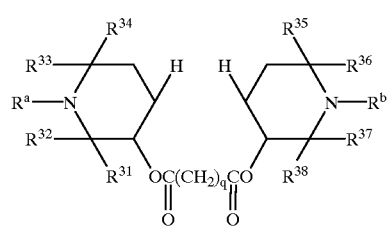

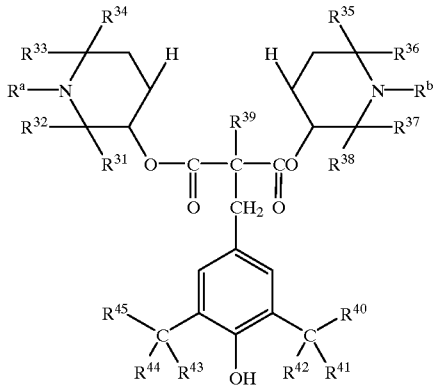

-continued

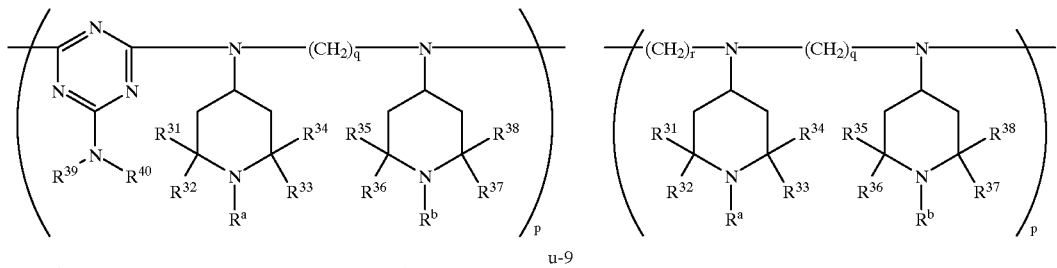

u-7 u-8

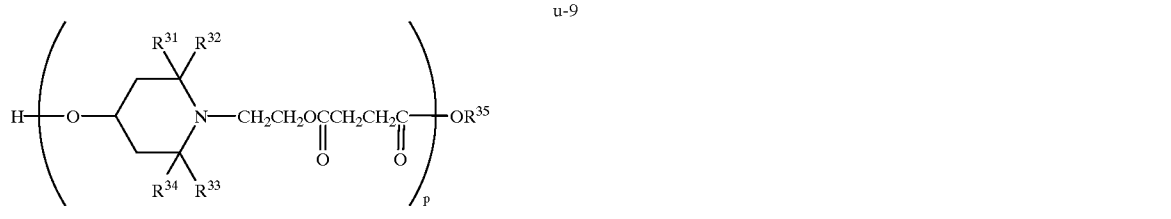

u-9 u-10

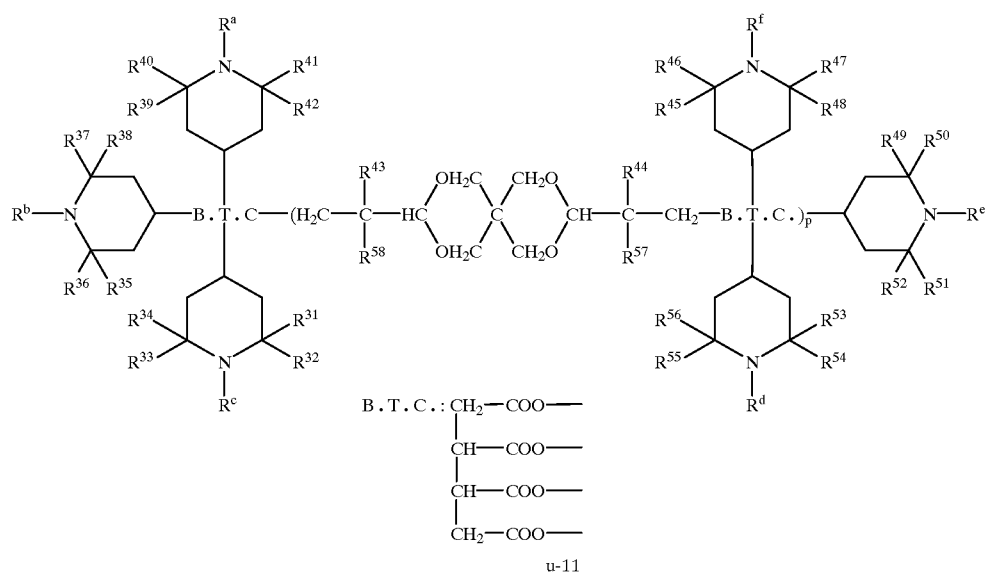

u-11 u-12

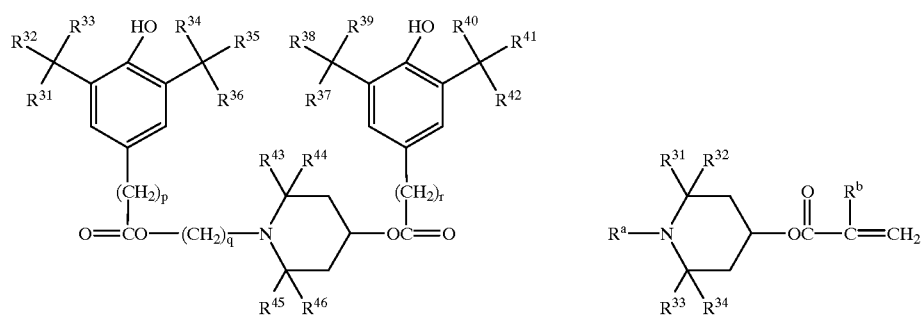

(In the above formulae u-5 to u-12, $R^{31}$ to $R^{58}$ are each an alkyl group; $R^a$ to $R^f$ are each a hydrogen atom or an alkyl group; and p, q and r are each a positive integer.)

In the above u-5 to u-12, there is no restriction as to the number of the carbon atoms of the alkyl group; generally, the number of the carbon atoms is preferably 1 to 12 in view of the general availability of compounds having such an alkyl group. The hindered amine light stabilizer may be Sumisorb LS-2000 and LS-2001 (trade names), manufactured by Sumitomo Chemical Co., Ltd.

Of the above ultraviolet stabilizers, those represented by the general formulae u-1, u-3, u-5, u-6, u-8, u-9, u-10, u-11 and u-12 can be preferably used to improve the durability of various photochromic compounds.

The above ultraviolet stabilizers are added preferably in an amount of 0.01 to 10,000 parts by weight, and particularly preferably, 10 to 500 parts by weight in view of the photochromic action of the resulting photochromic composition, based on 100 parts by weight of the fulgimide compound of the general formula (I).

There is also no restriction as to the method for producing the photochromic composition of the present invention. The individual components can be mixed in an arbitrary order.

There is also no restriction as to the method for curing the photochromic composition of the present invention to obtain a cured product, and known curing methods can be employed for this purpose. The photochromic composition of the present invention can be polymerized, either by the use of a radical polymerization initiator such as peroxide or azo compound, or by the irradiation of ultraviolet rays, α-ray, β-ray, γ-ray or the like, or by the combined use of the above two approaches. As the typical polymerization method, there can be used cast polymerization which comprises the steps of pouring the photochromic composition of the present invention that contains in advance a radical polymerization initiator into a mold supported by an elastomer gasket or a spacer, subjecting the composition to polymerization in a heating furnace, and removing the resulting polymer from the mold.

There is no restriction as to the radical polymerization initiator used, and known initiators can be used. As the typical initiators, there can be mentioned diallyl peroxides such as benzoyl peroxide, p-chlorobenzoyl peroxide, decanoyl peroxide, lauroyl peroxide, or acetyl peroxide; peroxy esters such as tert-butyl peroxy-2-ethylhexanate, tert-butyl peroxyneodecanate, cumyl peroxyneodecanate, tert-butyl peroxybenzoate, tert-butyl peroxyisobutyrate, or 1,1,3,3-tetramethylbutyl peroxy-2-ethylhexanate; percarbonates such as diisopropyl peroxycarbonate or di-sec-butyl peroxydicarbonate; and azo compounds such as azobisisobutyronitrile. Of these, the combination of tert-butyl peroxyneodecanate, tert-butyl peroxyneodecanate/tert-butyl peroxyisobutyrate and tert-butyl peroxyneodecanate/1,1,3,3-tetramethylbutyl peroxy-2-ethylhexanate is preferred in view of the polymerization efficiency and the hardness of the resulting cured product.

The fulgimide compound of the general formula (I) according to the present invention has remarkably improved photochromic action as compared with conventionally known fulgide compounds and fulgimide compounds, and hence gives a much higher color density in its color-developed state.

Therefore, the fulgimide compound of the present invention can be used as a photochromic material in a wide variety of applications. For example, the photochromic material can be used in various recording materials to supercede silver salt photosensitive materials, such as memory materials, copying materials, printing photosensitive materials, recording materials for cathode ray tube, photosensitive materials for laser and photosensitive material for holography. The photochromic material containing the compound of the present invention can also be used as a photochromic lens material, an optical filter material, a display material, an actinometer, or a decorative material. When the photochromic material is used, for example, for a photochromic lens, the photochromic lens may be produced by any methods as long as a lens having uniform light adjusting properties can be obtained. Stated more specifically, the photochromic lens can be obtained, for example, by sandwiching a polymer film in which the photochromic material of the present invention is uniformly dispersed between lenses; or by dissolving the photochromic compound, for example, in a silicone oil, impregnating the solution into the surface of the lens at 150 to 200° C. in 10 to 60 minutes, and further coating a curable substance thereon; or by applying the above-mentioned polymer film onto a lens substance first, and then coating the lens substance with a curable substance; or by dispersing the photochromic compound of the invention in a monomer capable of forming an organic lens and subjecting the mixture to polymerization to be cured.

EXAMPLES

Examples will be given to describe the present invention in more detail hereinafter, while it is by no means restricted to these Examples. In the Examples, "part(s)" means part(s) by weight.

Example 1

15.1 Grams (0.065 mol) of 4-acetyl-2-(4'-methoxyphenyl)thiophene and 20.0 g (0.065 mol) of diethyl 2-adamantylidenesuccinate were dissolved in 200 ml of toluene to obtain a solution. Then, 5.6 g of sodium hydride was dispersed in another 200 ml of toluene. Thereto was added the above solution. The resulting mixture was kept at 0° C. or below and stirred vigorously for 10 hours. An excess amount of an alcoholic aqueous solution of 10% potassium hydroxide was added to give rise to hydrolysis, followed by acidification with hydrochloric acid, to obtain dicarboxylic acid. The obtained dicarboxylic acid was treated with 100 ml of acetyl chloride, and then purified by silica gel column chromatography, to obtain 12 g of an acid anhydride of the following formula II-(1).

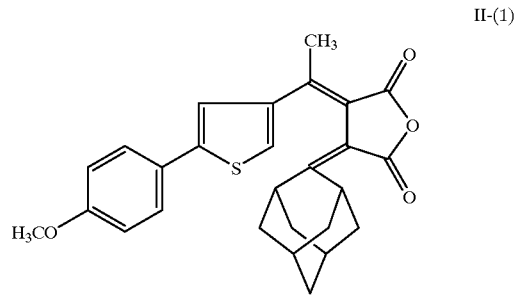

II-(1)

Thereafter, 5 g (11 mmol) of the above acid anhydride, 0.9 g of sodium hydride, and tetrahydrofuran were placed in a three-necked flask. Then, 2.7 g (22 mol) of an aniline compound of the following formula III-(1) was added dropwise.

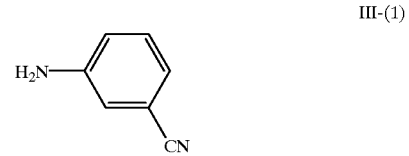

III-(1)

The resulting mixture was refluxed in a nitrogen atmosphere for 4 hours. After the completion of the reaction, the reaction mixture was fed into an aqueous solution of 10% hydrochloric acid and the resulting mixture was subjected to extraction with diethyl ether. After the solvent was removed, the residue was dissolved in dichloromethane, and 2.3 g (11 mmol) of dicyclohexylcarbodiimide was added thereto. The resulting mixture was stirred at room temperature for 3 hours, and then purified by silica gel column chromatography (eluent:dichloromethane). The resulting compound was heated in o-dichlorobenzene at 170° C. for 0.5 hour to convert into the following fulgimide compound I-(1). This compound was purified by silica gel column chromatography using hexane/chloroform mixture as an eluent, and obtained as pale yellow granular crystals from isopropyl alcohol and toluene in a yield of 17%. The elemental analysis of the compound gave C 74.90%, H 5.50%, N 5.03%, O 8.88% and S 5.77%, which very well agreed with the calculated values for $C_{34}H_{30}N_2O_3S$, i.e., C 74.70%, H 5.53%, N 5.12%, O 8.78% and S 5.86%. When the proton nuclear magnetic resonance spectrum (FIG. 1) of the compound was measured, the spectrum showed a peak of 9H based on the aromatic protons near δ7.0 to 7.5 ppm, a peak of 3H based on the protons of the methyl group at 4 position near δ3.8 ppm, a peak of 3H based on the protons of the methoxy group at 4 position near δ2.6 ppm, a peak of 1H based on the 1–5 shifted proton near δ4.0 ppm and a peak of 14H based on the protons of the 2-adamantylidene group near δ1.5 to 3.8 ppm.

Also, when the $^{13}C$-nuclear magnetic resonance spectrum ($^{13}C$-NMR) of the compound was measured, the spectrum showed a peak based on the carbon of the 2-adamantylidene group near δ27 to 70 ppm, a peak based on the carbon of the methyl group near δ15.7 ppm, a peak based on the aromatic carbon near δ110 to 160 ppm and a peak based on the carbon of the

bond near δ160 to 170 ppm.

From the above results, the isolated product was identified to be a fulgimide compound I-(1) represented by the following structural formula.

I-(1)

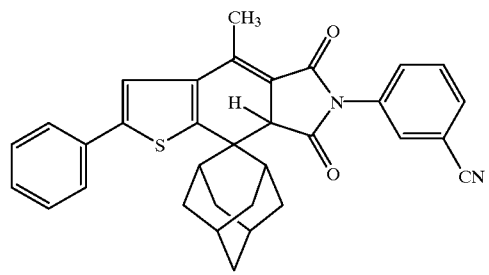

Examples 2 to 14

Fulgimide compounds of the following structural formulae I-(2) to I-(14) were synthesized in the same manner as in Example 1 except that the acid anhydride of the general formula (II) and the aniline compound of the general formula (III) used as raw materials were changed to those compounds corresponding to each of the following structural formulae I-(2) to I-(14).

Elemental analysis was conducted and proton nuclear magnetic resonance spectrum and $^{13}C$-nuclear magnetic resonance spectrum were measured for each compound synthesized in the same manner as in Example 1. As a result, the compounds represented by the following structural formulae I-(2) to I-(14) were identified. In Table 1 are shown the results of elemental analysis and values (calculated and obtained from structural formula) of these compounds and the characteristic chemical shift and the number of protons obtained from proton nuclear magnetic resonance spectrum.

I-(2)

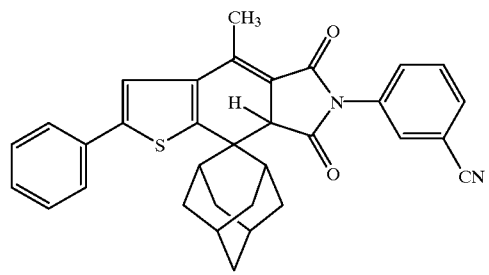

I-(3)

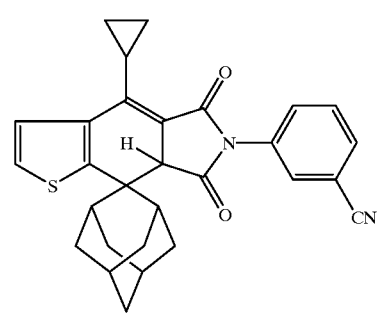

I-(4)

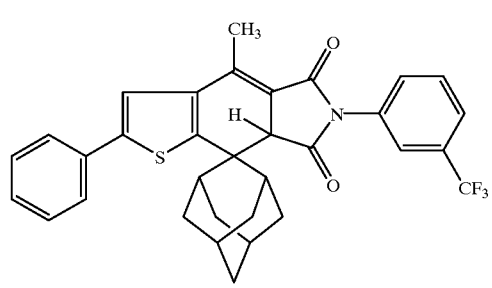

I-(5)

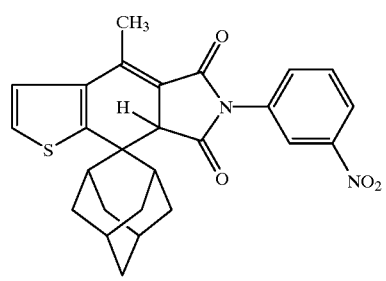

I-(6)

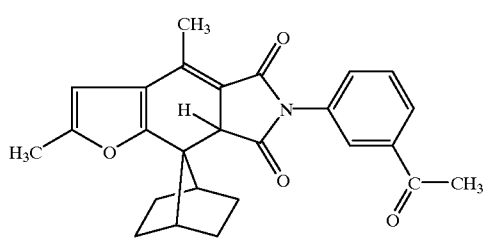

I-(7)
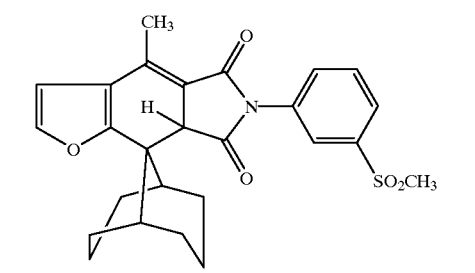
I-(8)
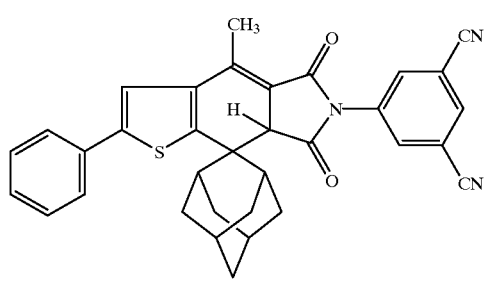
I-(9)
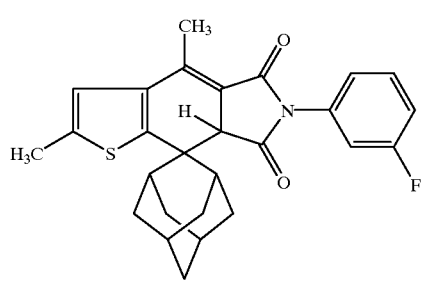
I-(10)
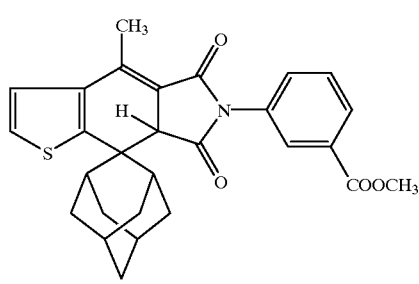
I-(11)
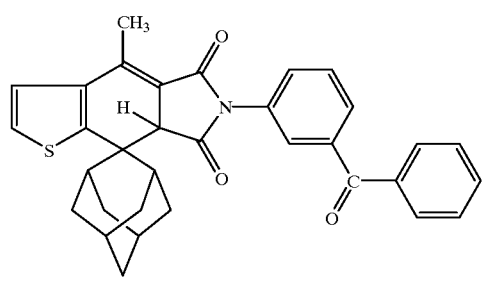
I-(12)
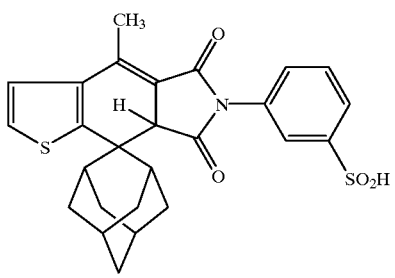
I-(13)
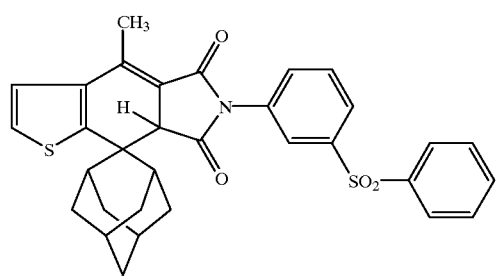
I-(14)
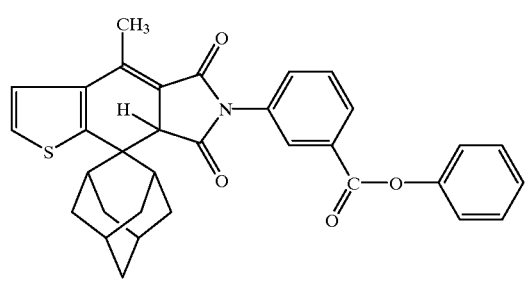
TABLE 1
| | Elemental analysis (%) | | | | | | | | | | | | |
| --- | --- | --- | --- | --- | --- | --- | --- | --- | --- | --- | --- | --- | --- |
| | Calculated values | | | | | | Found values | | | | | | H-NMR spectrum |
| Ex. | C | H | N | O | S | F | C | H | N | O | S | F | (ppm) |
| 2 | 76.72 | 5.46 | 5.42 | 6.19 | 6.21 | | 76.85 | 5.50 | 5.55 | 6.02 | 6.11 | | δ7.0~7.5:10H, δ3.9:1H, δ3.8:3H, δ3.8~1.5:14H |
| 3 | 74.65 | 5.62 | 6.00 | 6.86 | 6.87 | | 74.77 | 5.86 | 6.11 | 6.66 | 6.90 | | δ7.0~7.5:6H, δ4.0:1H, δ3.5~1.0:19H |
| 4 | 70.82 | 5.04 | 2.50 | 5.72 | 5.73 | 10.18 | 70.55 | 4.99 | 2.70 | 5.66 | 5.73 | 10.22 | δ7.0~7.5:10H, δ4.0:1H, δ3.8:3H, δ3.5~1.5:10H |
| 5 | 67.81 | 5.25 | 6.08 | 13.90 | 6.96 | | 67.98 | 5.35 | 6.03 | 14.02 | 7.04 | | δ7.0~7.8:6H, δ4.0:1H, δ3.8:3H, δ3.5~1.3:10H |

TABLE 1-continued

| | Elemental analysis (%) | | | | | | | | | | | H-NMR spectrum |
|---|---|---|---|---|---|---|---|---|---|---|---|---|
| | Calculated values | | | | | | Found values | | | | | |
| Ex. | C | H | N | O | S | F | C | H | N | O | S | F | (ppm) |
| 6 | 75.16 | 6.06 | 3.37 | 15.40 | 0.00 | | 75.32 | 5.96 | 3.15 | 15.44 | 0.00 | | δ6.5~7.5:5H, δ4.0:1H δ3.8~1.2:19H |
| 7 | 67.08 | 5.85 | 3.01 | 17.18 | 6.89 | | 67.03 | 5.77 | 2.98 | 17.29 | 6.93 | | δ6.5~7.8:6H, δ4.0:1H, δ3.8~1.2:20H |
| 8 | 75.39 | 5.02 | 7.76 | 5.91 | 5.92 | | 75.20 | 5.06 | 7.72 | 6.08 | 6.02 | | δ6.8~7.8:9H, δ4.1:1H, δ3.9:3H, δ3.8~1.5:14H |
| 9 | 72.46 | 5.86 | 3.13 | 7.15 | 7.16 | 4.24 | 72.27 | 5.68 | 3.02 | 7.29 | 7.22 | 4.22 | δ7.0~7.5:5H, δ4.0:1H, δ3.9:3H, δ3.6~1.3:17H |
| 10 | 71.01 | 5.75 | 2.96 | 13.51 | 6.77 | | 71.27 | 5.68 | 3.09 | 13.48 | 6.87 | | δ7.0~7.5:6H, δ4.0~1.3:21H |
| 11 | 76.27 | 5.62 | 2.70 | 9.24 | 6.17 | | 76.30 | 5.66 | 2.55 | 9.21 | 6.31 | | δ7.0~7.8:11H, δ4.0:1H, δ3.9:3H, δ3.6~1.3:14H |
| 12 | 65.11 | 5.25 | 2.92 | 13.34 | 13.37 | | 65.12 | 5.27 | 3.09 | 13.33 | 13.52 | | δ7.0~7.8:6H, δ4.0:1H, δ3.8:3H, δ3.5~1.2:14H |
| 13 | 69.16 | 5.26 | 2.52 | 11.52 | 11.54 | | 69.11 | 5.23 | 2.85 | 11.55 | 11.53 | | δ7.0~7.8:11H, δ4.0:1H, δ3.9:3H, δ3.5~1.2:14H |
| 14 | 74.00 | 5.46 | 2.61 | 11.95 | 5.99 | | 74.07 | 5.34 | 2.83 | 12.08 | 6.03 | | δ7.0~8.0:11H, δ4.0:1H, δ3.9:3H, δ3.4~1.2:14H |

Ex. = Example

Described below are the abbreviations and names of the compounds used in the following Examples.

I. Polymerizable monomers

3PG: tripropylene glycol dimethacrylate (trade name: NK Ester 3PG, a product of Shin Nakamura Chemical Co., Ltd.)

3G: triethylene glycol dimethacrylate (trade name: NK Ester 3G, a product of Shin Nakamura Chemical Co., Ltd.)

4G: tetraethylene glycol dimethacrylate (trade name: NK Ester 4G, a product of Shin Nakamura Chemical Co., Ltd.)

BPE-100N: 2,2-bis(4-methacryloyloxyethoxyphenyl) propane (trade name: NK Ester BPE-100, a product of Shin Nakamura Kagaku Kogyo K.K.)

BR-MA: 2,2-bis(4-methacryloyloxyethoxy-2,5-dibromophenyl)propane

MS: α-methylstyrene

MSD: α-methylstyrene dimer

HEMA: 2-hydroxyethyl methacrylate

BzMA: benzyl methacrylate

GMA: glycidyl methacrylate

II. Radical polymerization initiators

Perbutyl ND: tert-butyl peroxyneodecanate (trade name: Perbutyl ND, a product of Nippon Oils and Fats Co., Ltd.)

Perocta O: 1,1,3,3-tetramethylbutyl peroxy-2-ethylhexanate (trade name: Perocta O, a product of Nippon Oils and Fats Co., Ltd.)

III. Chromene compounds (1) spiro(norbornane-2,2'-(2H)benzo(h)chromene)

(2) spiro(bicyclo[3.3.1]nonane-9,2'-(2H)benzo(h)chromene)

(3) 7'-methoxyspiro(bicyclo(3.3.1)nonane-9,2'-(2H)benzo(h)chromene)

(4) 7'-methoxyspiro(norbornane-2,2'-(2H)benzo(h)chromene)

(5) 2,2-dimethyl-7-octoxy(2H)benzo(f)chromene (6) 2,2-(2'-difuryl)(2H)benzo(f)chromene (7) 2,2-(phenyl-2'-furyl)(2H)benzo(f)chromene (8) 9-morpholino-2,2-bis(3-fluoro-4-methoxyphenyl)(2H)benzo(f)chromene (9) 2,2-((2'-(3'-fluoronaphthyl)-2'-thienyl)(2H)benzo(f)chromene IV. Spirooxazine compounds (1) 1',5'-dimethyl-6'-fluoro-6"-morpholinodispiro(cyclohexane-1,3'-(3H)indole-2'-(2H),3"-(3H)naphtho(3,2-a)(1,4)oxazine (2) 6'-fluoro-1'-methoxycarbonylethyl-8"-methoxy-6"-piperidinodispiro(cyclohexane-1,3'-(3H)indole-2'-(2H),3"-(3H)naphtho(3,2-a)(1,4)oxazine (3) 1'-isobutyl-5'-methyl-6'-fluoro-6"-morpholinodispiro(cyclohexane-1,3'-(3H)indole-2'-(2H),3"-(3H)naphtho(3,2-a)(1,4)oxazine V. Fulgimide compounds other than those used in the present invention The compounds of the following formulae (A) to (F) were used.

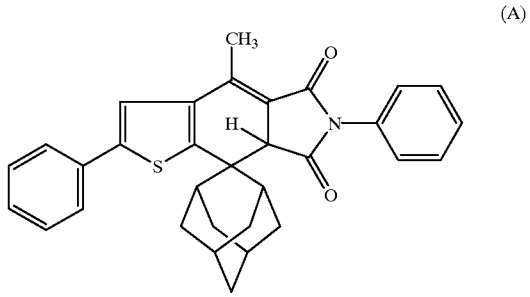

(A)

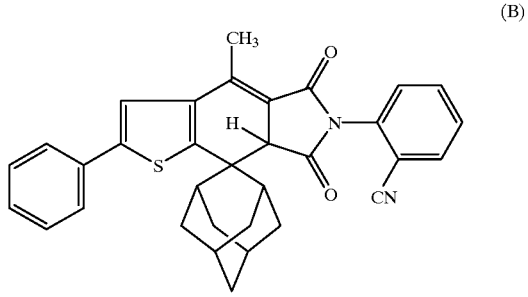

(B)

-continued
(C)
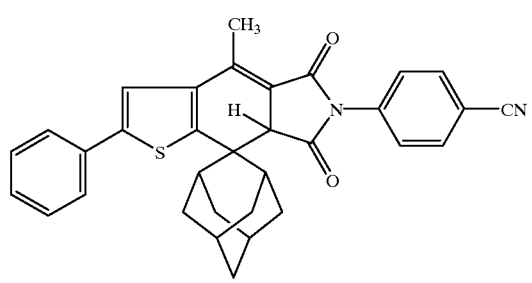
(D)
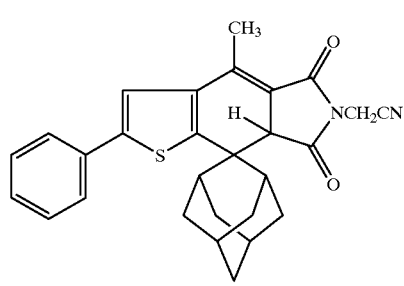
(E)
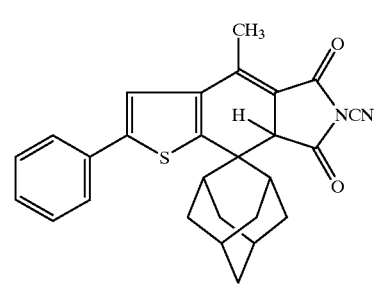
(F)
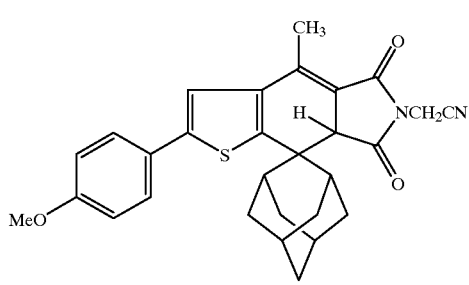
VI. Ultraviolet absorber (abbreviated as UVA hereinafter)
Tinuvin P: 2-(5-methyl-2-hydroxyphenyl)benzotriazole (a product of Ciba-Geigy Japan Limited)
VII. Ultraviolet stabilizers
(1) Sanol LS-2626 (trade name, a product of Sankyo Co.)
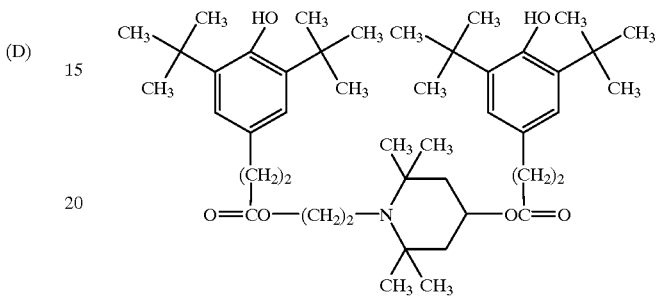
(2) Mark LA-87 (trade name, Adeka-Agas Corp.
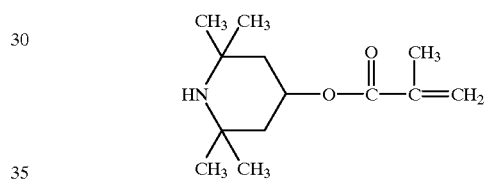
(3) Irgastab 2002 (trade name, a product of Ciba-Geigy Japan Limited)
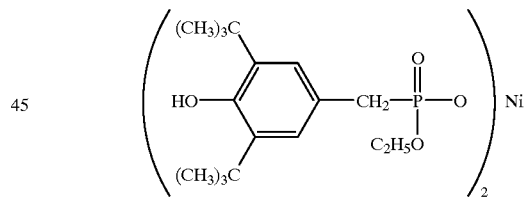

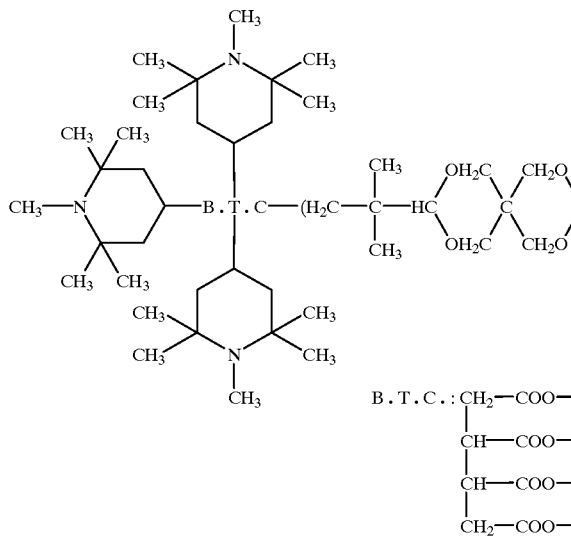
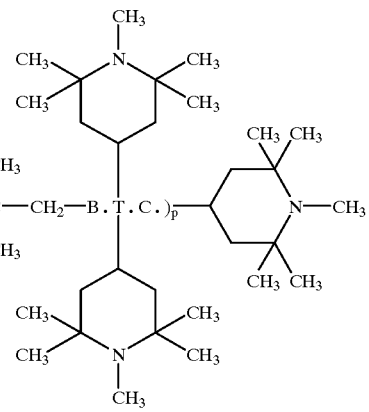
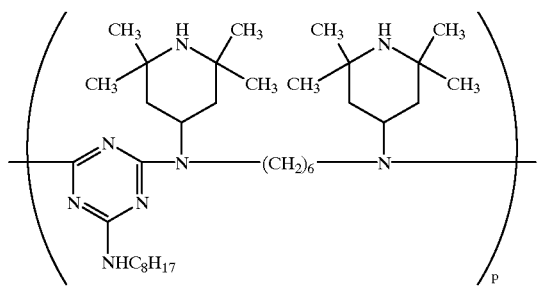

(5) Chimasorb 044 (trade name, a product of Ciba-Geigy Japan Limited)

$$\left( \begin{array}{c} \text{structure with piperidine groups, triazine ring, } (CH_2)_6, \text{ and } NHC_8H_{17} \end{array} \right)_p$$

Example 15

To 100 parts by weight of a polymerizable monomer consisting of 45 parts by weight of 4G, 45 parts by weight of 3PG, 9 parts by weight of GMA and 1 part by weight of MSD were added 0.05 part by weight of fulgimide compound I-(1) and 1 part by weight of Perbutyl ND as a polymerization catalyst. The solution was stirred thoroughly until the content thereof was completely dissolved. The solution was poured into a mold constituted by a glass plate and a gasket composed of an ethylene-vinyl acetate copolymer. The mold was placed in an air oven and the solution therein was subjected to polymerization at 35 to 90° C. for 20 hours. After the completion of the polymerization, the obtained photochromic cured product was removed from the glass plate of the mold.

The obtained photochromic cured product having a thickness of 2 mm was exposed to the light emitted from a xenon lamp, model L-2480 (300 W) SHL-100, manufactured by Hamamatsu Photonics, through Aero Mass Filter (a product of Corning Co.), at 20±1° C. for 120 seconds at a beam intensity (on the polymer surface of 365 nm=2.4 mW/cm$^2$ and 254 nm=24 $\mu$W/cm$^2$, whereby the cured product was allowed to develop a color. A value [$\epsilon$ (120 seconds)–$\epsilon$ (0 seconds)] was calculated and taken as the "color density" of the developed color. In the above expression, $\epsilon$ (120 seconds) is an absorbance at maximum absorption wavelength after 120 seconds of irradiation, and $\epsilon$ (0 seconds) is an absorbance at maximum absorption wavelength under no irradiation.

The color-developed cured product obtained above was measured for fatigue life by the use of a xenon long-life fadeometer, model FAL-25AX-HC, manufactured by Suga Testing Instrument Co., Ltd.. Fatigue life (T½) was expressed by the time required to decrease the color density of fulgimide compound to half of its initial value. The results are shown in Table 2.

Examples 16 to 28

The procedure of Example 15 was repeated with the fulgimide compounds I-(2) to I-(14) to obtain photochromic cured products and the photochromic cured products were measured for color density of developed color and fatigue life. The results are shown in Table 2.

Examples 29 to 32

The procedure of Example 15 was repeated except that the composition of the polymerizable monomer was changed as shown in Table 2. The results are shown in Table 2.

Comparative Examples 1 to 6

For comparison, photochromic cured products were prepared with fulgimide compounds (A) to (F) other than those used in the present invention, and the photochromic cured products were measured for color density of developed color and fatigue life. The results are shown in Table 2.

TABLE 2

| Ex. | Fulgimide compound No. | Polymerizable monomers (parts) | Color density (Abs) | λ max (nm) | T½ (hours) |
|---|---|---|---|---|---|
| 15 | I-(1) | 3PG:45,4G:45,GMA:9,MSD:1 | 1.33 | 582 | 98 |
| 16 | I-(2) | 3PG:45,4G:45,GMA:9,MSD:1 | 1.25 | 570 | 105 |
| 17 | I-(3) | 3PG:45,4G:45,GMA:9,MSD:1 | 1.42 | 560 | 255 |
| 18 | I-(4) | 3PG:45,4G:45,GMA:9,MSD:1 | 1.22 | 566 | 88 |
| 19 | I-(5) | 3PG:45,4G:45,GMA:9,MSD:1 | 1.36 | 572 | 108 |
| 20 | I-(6) | 3PG:45,4G:45,GMA:9,MSD:1 | 1.06 | 525 | 88 |
| 21 | I-(7) | 3PG:45,4G:45,GMA:9,MSD:1 | 1.20 | 530 | 112 |
| 22 | I-(8) | 3PG:45,4G:45,GMA:9,MSD:1 | 1.58 | 582 | 96 |
| 23 | I-(9) | 3PG:45,4G:45,GMA:9,MSD:1 | 1.43 | 574 | 76 |
| 24 | I-(10) | 3PG:45,4G:45,GMA:9,MSD:1 | 1.14 | 550 | 105 |
| 25 | I-(11) | 3PG:45,4G:45,GMA:9,MSD:1 | 1.18 | 563 | 107 |
| 26 | I-(12) | 3PG:45,4G:45,GMA:9,MSD:1 | 1.22 | 567 | 76 |
| 27 | I-(13) | 3PG:45,4G:45,GMA:9,MSD:1 | 1.25 | 564 | 120 |
| 28 | I-(14) | 3PG:45,4G:45,GMA:9,MSD:1 | 1.12 | 562 | 108 |
| 29 | I-(1) | 4G:65,3G:15,GMA:9,MS:8,HEMA:2,MSD:1 | 1.28 | 584 | 104 |
| 30 | I-(1) | BR-MA:20,BzMA:25,3PG:37,GMA:9,MS:8,MSD:1 | 1.29 | 590 | 110 |
| 31 | I-(1) | BPE-100N:45,3G:37,GMA:9,MS:8,MSD:1 | 1.11 | 590 | 92 |
| 32 | I-(1) | 4G:100 | 1.41 | 584 | 10 |
| C. Ex. 1 | A | 3PG:45,4G:45,GMA:9,MSD:1 | 0.51 | 555 | 90 |
| C. Ex. 2 | B | 3PG:45,4G:45,GMA:9,MSD:1 | 0.64 | 570 | 78 |
| C. Ex. 3 | C | 3PG:45,4G:45,GMA:9,MSD:1 | 0.63 | 570 | 100 |
| C. Ex. 4 | D | 3PG:45,4G:45,GMA:9,MSD:1 | 0.72 | 568 | 90 |
| C. Ex. 5 | E | 3PG:45,4G:45,GMA:9,MSD:1 | 0.74 | 620 | 83 |
| C. Ex. 6 | F | 3PG:45,4G:45,GMA:9,MSD:1 | 0.78 | 578 | 85 |

Ex. = Example
C. Ex. = Comparative Example

It is clear from Table 2 that the fulgimide compounds of the present invention have remarkably high color densities in a color-developed state, as compared with conventional fulgimide compounds.

Example 33

A photochromic cured product was obtained in the same manner as in Example 15 except that 0.05 part of (1) Sanol LS-2626 was added as an ultraviolet stabilizer. The obtained cured product was measured in the same manner as in Example 15. The results are shown in Table 3.

Examples 34 to 46

The procedure of Example 33 was repeated except that the fulgimide compound of the present invention and the ultraviolet stabilizer were changed. The results are shown in Table 3.

It is clear from Table 3 that fatigue lives of the compounds listed herein are improved by the addition of ultraviolet stabilizer, as compared with Examples of Table 2.

TABLE 3

| Ex. | Fulgimide compound No. | Ultraviolet stabilizer No | Ultraviolet stabilizer Amount (parts) | T½ (hours) |
|---|---|---|---|---|
| 33 | I-(1) | (1) | 0.05 | 150 |
| 34 | I-(1) | (1) | 1.0 | 255 |
| 35 | I-(1) | (2) | 0.5 | 174 |
| 36 | I-(1) | (3) | 0.4 | 165 |
| 37 | I-(1) | (4) | 0.7 | 180 |
| 38 | I-(1) | (5) | 0.5 | 188 |
| 39 | I-(2) | (1) | 0.05 | 166 |
| 40 | I-(2) | (2) | 1.0 | 189 |
| 41 | I-(2) | (5) | 0.5 | 206 |
| 42 | I-(3) | (1) | 0.5 | 403 |
| 43 | I-(3) | (2) | 0.7 | 408 |
| 44 | I-(3) | (3) | 0.7 | 411 |
| 45 | I-(4) | (1) | 0.5 | 166 |
| 46 | I-(4) | (2) | 2.0 | 234 |

Example 47

A photochromic cured product was obtained in the same manner as in Example 15 except that the photochromic compound was changed to 0.04 part of a chromene compound (2), 0.03 part of the fulgimide compound I-(1) of the present invention and 0.05 part of a spirooxazine compound (1).

The obtained photochromic cured product was measured for color density of developed color and color shift after a long-term use.

Specifically, an unused photochromic cured product was first exposed to the light emitted from a xenon lamp, model L-2480 (300 W) SHL-100, manufactured by Hamamatsu Photonics, through Aero Mass Filter (a product of Corning Co.), at 20±1° C. for 120 seconds at a beam intensity (on the cured product surface) of 365 nm=2.4 mW/cm$^2$ and 254 nm=24 μW/cm$^2$, whereby the cured product was allowed to develop a color, and measured for initial color spectrum ($T_0$).

Then, a cycle comprising the steps of exposing the photochromic cured product to sunlight for 30 minutes for color development and subjecting it to color fading for 1 hour under a fluorescent lamp was repeated three times a day. This test was conducted 30 days in all. The photochromic cured product after the completion of the test was measured for initial color spectrum ($T_{30}$).

In each of the initial color spectra ($T_0$) and ($T_{30}$), the maximum absorption wavelength absorbance at 450 to 470 nm and the maximum absorption wavelength absorbance at 580 to 590 nm were measured. The maximum absorption wavelength absorbance at 450 to 470 nm indicates a yellow color density and the maximum absorption wavelength absorbance at 580 to 590 nm indicates a blue color density. Using these measurement values, the "color density" and "color shift" defined by the following formulae were determined.

Initial color density (Abs.)=blue color density at $T_0$

Color shift (%)=yellow durability (%)−blue durability (%)

In the above formulae, yellow durability and blue durability are defined by the following formulae.

Yellow durability (%)=(yellow color density at $T_{30}$)/(yellow color density at $T_0$)×100

Blue durability (%)=(blue color density at $T_{30}$)/(blue color density at $T_0$)×100

Also, the photochromic cured product of $T_0$ and the photochromic cured product of $T_{30}$ were each allowed to develop a color under sunlight, and the developed colors were evaluated with naked eyes. As a result, the initial color density was 0.88 and the color shift was 5%. The results are shown in Table 4.

Examples 48 to 55

The procedure of Example 47 was repeated except that the chromene compound, the fulgimide compound of the present invention, the spirooxazine compound and the ultraviolet absorber were changed as shown in Table 4. The results are shown in Table 4.

Example 56

The procedure of Example 47 was repeated except that the polymerizable monomer composition was changed to one comprising 60 parts of 4G, 15 parts of 3G, 5 parts of HEMA, 10 parts of GMA, 9 parts of MS and 1 part of MSD. The results are shown in Table 4.

Examples 57 to 61

The procedure of Example 56 was repeated except that the chromene compound, the fulgimide compound of the present invention, the spirooxazine compound and the ultraviolet absorber were changed as shown in Table 4. The results are shown in Table 4.

Comparative Examples 7 and 8

Initial color density and color shift were obtained in the same manner as in Example 47 for formulations shown in Table 4 except that known fulgimide compounds (F) and (D) were used in place of the fulgimide compound of the present invention. The results are shown in Table 4.

As is clear from the comparison of Example 47 with Comparative Example 7, an initial color density obtained in Example 47 was equal to that of Comparative Example 7, although the amount of the fulgimide compound of the present invention used in Example 47 was only ½ or less of the amount of the fulgimide compound used in Comparative Example 7.

In Comparative Example 8 where the same amount of fulgimide compound as in Example 47 was used, the initial color density obtained was about a half of that of Example 47.

TABLE 4

| | Chromene compound | | Fulgimide compound (present invention) | | Spiro-oxazine compound | | UVA | |
|---|---|---|---|---|---|---|---|---|
| Ex. | No | Amount (parts) | No | Amount (parts) | No | Amount (parts) | No | Amount (parts) |
| 47 | (2) | 0.04 | I-(1) | 0.03 | (1) | 0.05 | — | — |
| 48 | (2) | 0.045 | I-(1) | 0.05 | (1) | 0.05 | — | — |
| 49 | (2) | 0.05 | I-(1) | 0.03 | (1) | 0.07 | — | — |
| 50 | (2.)/(3.) | 0.02/0.055 | I-(2) | 0.025 | (1) | 0.05 | — | — |
| 51 | (1.)/(4.) | 0.02/0.05 | I-(3) | 0.025 | (1) | 0.05 | — | — |
| 52 | (5) | 0.06 | I-(4) | 0.03 | (2) | 0.04 | — | — |
| 53 | (8) | 0.025 | I-(1) | 0.025 | (1) | 0.05 | — | — |
| 54 | (8.)/(9.) | 0.02/0.05 | I-(8) | 0.025 | (1) | 0.03 | — | — |
| 55 | (2) | 0.07 | I-(1) | 0.03 | (1) | 0.05 | 1 | 0.03 |
| 56 | (2) | 0.07 | I-(1) | 0.03 | (1) | 0.05 | — | — |
| 57 | (8) | 0.025 | I-(1) | 0.025 | (1) | 0.05 | — | — |
| 58 | (6) | 0.05 | I-(5) | 0.03 | (1) | 0.04 | — | — |
| 59 | (8) | 0.05 | I-(1) | 0.05 | (1) | 0.1 | — | — |
| 60 | (7) | 0.03 | I-(8) | 0.03 | (3) | 0.03 | — | — |
| 61 | (2) | 0.07 | I-(1) | 0.03 | (1) | 0.05 | 1 | 0.03 |

| | Chromene compound | | Known fulgimide compound | | Spiro-oxazine compound | | UVA | |
|---|---|---|---|---|---|---|---|---|
| C. Ex. | No | Amount (parts) | No | Amount (parts) | No | Amount (parts) | No | Amount (parts) |
| 7 | (2) | 0.05 | (F) | 0.07 | (1) | 0.055 | — | — |
| 8 | (2.)/(3.) | 0.015/0.035 | (F.)/(D.) | 0.015/0.015 | (1) | 0.05 | — | — |

TABLE 4-continued

| Ex. | T0 color | Initial color density (Abs) | T30 color | Color shift (%) | Fulgimide/spiro-oxazine (wt %) |
|---|---|---|---|---|---|
| 47 | gray | 0.88 | gray | 5 | 0.60 |
| 48 | gray | 1.15 | gray | 10 | 1.00 |
| 49 | gray | 0.92 | gray | 3 | 0.43 |
| 50 | brown | 0.83 | brown | 5 | 0.50 |
| 51 | brown | 0.86 | brown | 5 | 0.50 |
| 52 | brown | 0.84 | brown | 7 | 0.75 |
| 53 | gray | 0.82 | gray | 5 | 0.50 |
| 54 | brown | 0.81 | brown | 7 | 0.67 |
| 55 | gray | 0.90 | gray | 0 | 0.60 |
| 56 | gray | 0.90 | gray | 4 | 0.60 |
| 57 | gray | 0.83 | gray | 6 | 0.50 |
| 58 | brown | 0.81 | brown | 8 | 0.75 |
| 59 | gray | 1.20 | gray | 7 | 0.50 |
| 60 | brown | 0.90 | brown | 7 | 1.00 |
| 61 | gray | 0.93 | gray | −2 | 0.60 |

| C.Ex. | T0 color | Initial color density (Abs) | T30 color | Color shift (%) | Fulgimide/spiro-oxazine (wt %) |
|---|---|---|---|---|---|
| 7 | gray | 0.82 | | | |
| 8 | brown | 0.42 | | | |

Example 62

The procedure of Example 47 was repeated except that the polymerizable monomer was changed to 70 parts of BPE-100N, 20 parts of BzMA, 9 parts of GMA and 1 part of MSD and the polymerization catalyst was changed to Perbutyl ND/Perocta O=0.5/0.4 part by weight. As a result, an initial color density was 0.86 and a color shift was 6%.

Examples 63 to 70

The procedure of Example 62 was repeated except that the chromene compound, the fulgimide compound of the present invention, the spirooxazine compound and the ultraviolet absorber were changed as shown in Table 5. The results are shown in Table 5.

TABLE 5

| | Chromene compound | | Fulgimide compound | | Spiro-oxazine compound | | UVA | |
|---|---|---|---|---|---|---|---|---|
| Ex. | No | Amount (parts) | No | Amount (parts) | No | Amount (parts) | No | Amount (parts) |
| 62 | (2) | 0.04 | I-(1) | 0.03 | (1) | 0.05 | — | — |
| 63 | (2) | 0.045 | I-(1) | 0.05 | (1) | 0.05 | — | — |
| 64 | (2) | 0.05 | I-(1) | 0.03 | (1) | 0.07 | — | — |
| 65 | (2.)/(3.) | 0.02/0.055 | I-(2) | 0.025 | (1) | 0.05 | — | — |
| 66 | (1.)/(4.) | 0.02/0.05 | I-(3) | 0.025 | (1) | 0.05 | — | — |
| 67 | (5) | 0.06 | I-(4) | 0.03 | (2) | 0.04 | — | — |
| 68 | (6) | 0.05 | I-(5) | 0.03 | (1) | 0.04 | — | — |
| 69 | (8) | 0.05 | I-(1) | 0.05 | (1) | 0.1 | — | — |
| 70 | (2) | 0.07 | I-(1) | 0.03 | (1) | 0.05 | 1 | 0.03 |

| Ex. | T0 color | Initial color density (Abs) | T30 color | Color shift (%) | Fulgimide/spirooxazine (wt %) |
|---|---|---|---|---|---|
| 62 | gray | 0.86 | gray | 6 | 0.60 |
| 63 | gray | 1.20 | gray | 5 | 1.00 |
| 64 | gray | 0.89 | gray | 2 | 0.43 |
| 65 | brown | 0.79 | brown | 2 | 0.50 |
| 66 | brown | 0.85 | brown | 2 | 0.50 |
| 67 | brown | 0.86 | brown | 5 | 0.75 |
| 68 | brown | 0.82 | brown | 2 | 0.75 |
| 69 | gray | 1.22 | gray | 1 | 0.50 |
| 70 | gray | 0.93 | gray | −3 | 0.60 |

Figure 1:
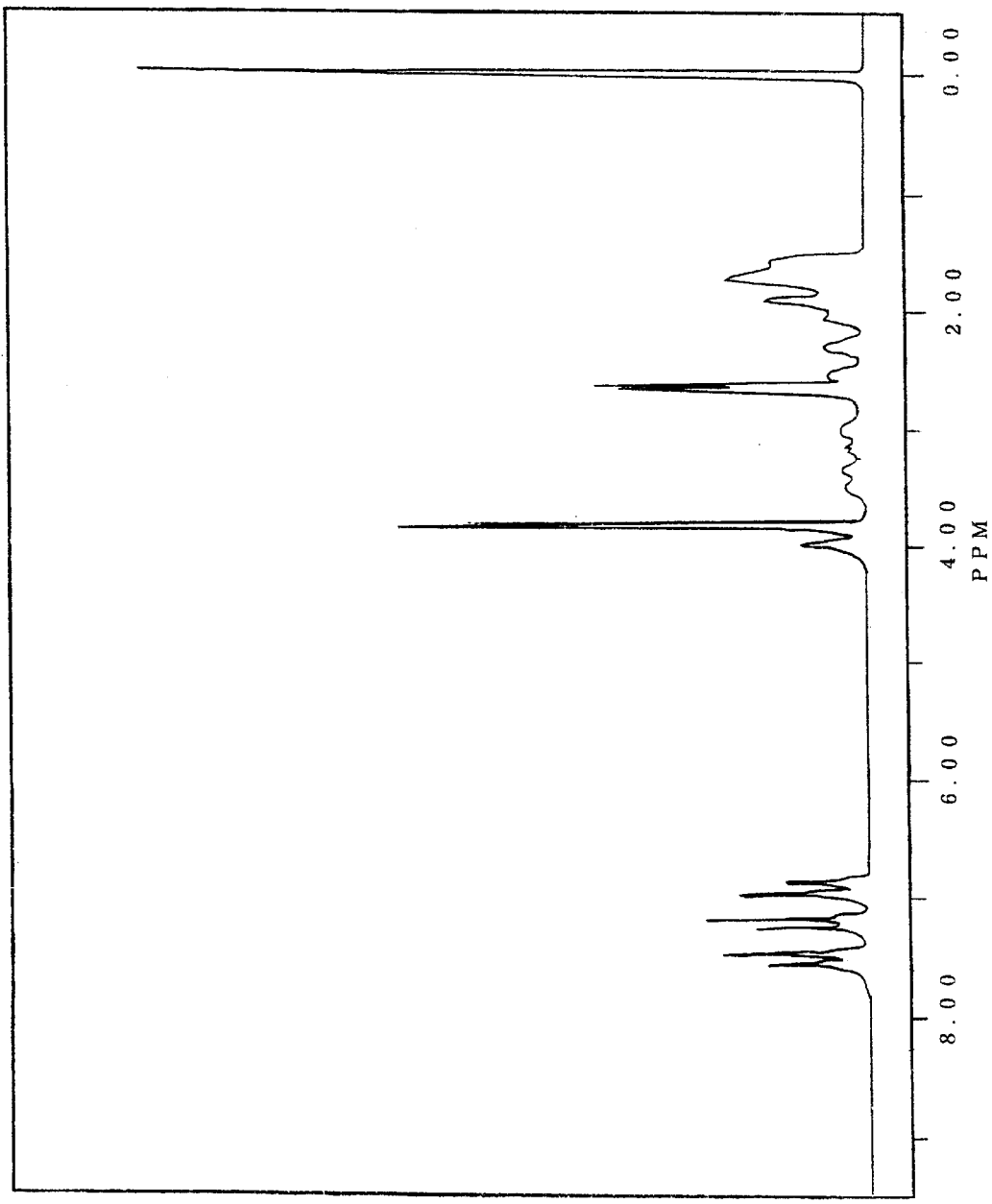
FIG. 1 is a chart of a $^1$H-nuclear magnetic resonance spectrum of the fulgimide compound obtained in Example 1.

What is claimed is:

1. A fulgimide compound represented by the following general formula (I):

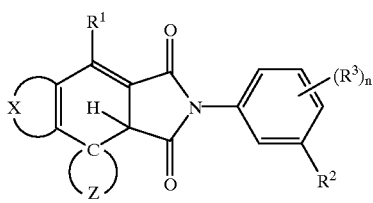

wherein
the following group (a)

is a divalent aromatic hydrocarbon group or a divalent unsaturated heterocyclic group, each of which may have a substituent(s), said divalent unsaturated heterocyclic group being a 5- or 6-membered unsaturated hetero-monocyclic group having 1 to 3 hetero atoms of at least one kind selected from the group consisting of nitrogen atom, oxygen atom and sulfur atom, or a fused unsaturated heterocyclic group in which a benzene ring or a cyclohexene ring is fused to a 5- or 6-membered unsaturated hetero-monocyclic group having 1 to 3 hetero atoms of at least one kind selected from the group consisting of nitrogen atom, oxygen atom and sulfur atom;

the following group (b)

is a norobornylidene group, a bicyclo(3.3.1)nonylidene group or an adamantylidene group, each of which may have a substituent(s);

$R^1$ is a monovalent hydrocarbon group which may have a substituent(s);

$R^2$ is an electron-attracting group;

$R^3$ is an alkyl group, an aryl group, an amino group, an alkoxy group or an electron-attracting group;

n is an integer of 0 to 4; and when n is an integer of 2 or more, a plurality of $R^3$s can be atoms or groups, which are different from each other.

2. The fulgimide compound of claim 1, wherein, in the general formula (I), the group (a) is a divalent aromatic hydrocarbon group having 6 to 20 carbon atoms.

3. The fulgimide compound of claim 1, wherein, in the general formula (I), the group (a) is a divalent aromatic hydrocarbon group or a divalent unsaturated heterocyclic group, each of which may be substituted by 1 to 3 atoms or groups selected from the group consisting of a halogen atom, nitro group, cyano group, amino group, an alkyl group having 1 to 4 carbon atoms, an alkoxy group having 1 to 4 carbon atoms, an alkylthio group having 1 to 4 carbon atoms, an aryl group having 6 to 10 carbon groups and an aralkoxy group having 7 to 15 carbon atoms.

4. The fulgimide compound of claim 1, wherein, in the general formula (I), the group (a) is a 5- or 6-membered divalent hetero-monocyclic group having one nitrogen, oxygen or sulfur atom, which may be substituted by 1 to 3 atoms or groups selected from the group consisting of a halogen atom, nitro group, cyano group, amino group, an alkyl group having 1 to 4 carbon atoms, an alkoxy group having 1 to 4 carbon atoms, an alkylthio group having 1 to 4 carbon atoms, an aryl group having 6 to 10 carbon groups and an aralkoxy group having 7 to 15 carbon atoms.

5. The fulgimide compound of claim 1, wherein, in the general formula (I), the group (b) is an adamantylidene group which may have a substituent(s).

6. The fulgimide compound of claim 1, wherein, in the general formula (I), $R^1$ is an alkyl group having 1 to 20 carbon atoms, a cycloalkyl group having 3 to 8 carbon atoms, an aryl group having 6 to 14 carbon atoms or an aralkyl group having 7 to 10 carbon atoms, each of which may have a substituent(s).

7. The fulgimide compound of claim 1, wherein, in the general formula (I), $R^1$ is an alkyl group having 1 to 6 carbon atoms or a cycloalkyl group having 3 to 6 carbon atoms, each of which may have a substituent(s).

8. The fulgimide compound of claim 1, wherein, in the general formula (I), $R^3$ is an alkyl group having 1 to 6 carbon atoms, an aryl group having 6 to 14 carbon atoms, an alkylamino group having 1 to 5 carbon atoms, an alkoxy group having 1 to 4 carbon atoms, a halogen atom, a perhalogenoalkyl group, a cyano group, a substituted or unsubstituted alkoxycarbonyl group, a substituted or unsubstituted alkylcarbonyl group, a substituted or unsubstituted arylcarbonyl group, a nitro group, a sulfonyl group, a substituted or unsubstituted alkylsulfonyl group, a substituted or unsubstituted arylsulfonyl group, or a substituted or unsubstituted aryloxycarbonyl group.

9. The fulgimide compound of claim 1, wherein, in the general formula (I), n is 0; $R^1$ is a substituted or unsubstituted alkyl group or cycloalkyl group; the electron-attracting group represented by $R^2$ is a halogen atom, a perhalogenoalkyl group, a cyano group, a substituted or unsubstituted alkoxycarbonyl group, a substituted or unsubstituted alkylcarbonyl group, a substituted or unsubstituted arylcarbonyl group, a nitro group, a sulfonyl group, a substituted or unsubstituted alkylsulfonyl group, a substituted or unsubstituted arylsulfonyl group, or a substituted or unsubstituted aryloxycarbonyl group; the group (a) is a divalent unsaturated heterocyclic group which may have a substituent(s); and the group (b) is an admantylidene group.

10. A polymerizable photochromic composition comprising 100 parts by weight of a polymerizable monomer and 0.001 to 10 parts by weight of the fulgimide compound of claim 1.

11. The polymerizable photochromic composition of claim 10, wherein the polymerizable monomer is composed of 100 parts by weight of a radical-polymerizable monomer and 1 to 30 parts by weight of a polymerizable monomer comprising molecules each having at least one epoxy group.

12. The polymerizable photochromic composition of claim 10, further comprising 0.01 to 0.2 part by weight of a chromene compound and/or a spirooxazine compound, based on 100 parts by weight of the polymerizable monomer.

13. The polymerizable photochromic composition of claim 10, further comprising 0.01 to 10,000 parts by weight of an ultraviolet stabilizer, based on 100 parts by weight of the fulgimide compound.

14. The polymerizable photochromic composition of claim 10, comprising:

(1) a polymerizable monomer composed of 100 parts by weight of a radical-polymerizable monomer and 1 to 30 parts by weight of a polymerizable monomer comprising molecules each having at least one epoxy group, and (2) 0.01 to 0.05 part by weight of the fulgimide compound of claim 1, 0.01 to 0.2 part by weight of a chromene compound and 0.03 to 0.1 part by weight of a spirooxazine compound, based on 100 parts by weight of the polymerizable monomer, the weight ratio of the fulgimide compound/the spirooxazine compound being 1 or less.

15. A photochromic lens made of a polymer formed from the photochromic composition of claim 10.

16. A fulgimide compound represented by the following general formula (I):

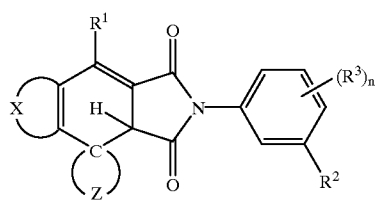

(I)

wherein
the following group (a)

(a)

is a divalent aromatic hydrocarbon group or a divalent unsaturated heterocyclic group, each of which may have a substituent(s), said divalent unsaturated heterocyclic group being a 5- or 6-membered unsaturated hetero-moncyclic group having 1 to 3 hetero atoms of at least one kind selected from the group consisting of nitrogen atom, oxygen atom and sulfur atom, or a fused unsaturated heterocyclic group in which a benzene ring or a cyclohexene ring is fused to a 5- or 6-membered unsaturated hetero-moncyclic group having 1 to 3 hetero atoms of at least one kind selected from the group consisting of nitrogen atom, oxygen atom and sulfur atom;

the following group (b)

(b)

is a norobornylidene group, a bicyclo(3.3.1)nonylidene group or an adamantylidene group, each of which may have a substituent(s);

$R^1$ is a monovalent hydrocarbon group which may have a substituent(s);

$R^2$ is a halogen atom, a perhalogenoalkyl group, a cyano group, a substituted or unsubstituted alkoxycarbonyl group, a substituted or unsubstituted alkylcarbonyl group, a substituted or unsubstituted arylcarbonyl group, a nitro group, a sulfonyl group, a substituted or unsubstituted alkylsulfonyl group, a substituted or unsubstituted arylsulfonyl group or a substituted or unsubstituted aryloxycarbonyl group;

$R^3$ is an alkyl group, an aryl group, an amino group, an alkoxy group or an electron-attracting group;

n is an integer of 0 to 4; and when n is an integer of 2 or more, a plurality of $R^3$s can be atoms or groups, which are different from each other.

* * * * *